United States Patent
Dietrich et al.

(10) Patent No.: US 9,441,243 B2
(45) Date of Patent: Sep. 13, 2016

(54) IMPORTATION OF A RIBOZYME INTO VEGETABLE MITOCHONDRIA BY A PSEUDO-TRNA THAT CAN BE AMINOACYLATED BY VALINE

(75) Inventors: André Dietrich, Oberschaeffolsheim (FR); Romain Val, Mantes la Jolie (FR); Clarisse Valentin, Strasbourg (FR); Theo Dreher, Corvallis, OR (US); Jan Barciszewski, Poznan (PL); Maciej Szymanski, Poznan (PL); Eliza Wyszko, Poznan (PL)

(73) Assignee: Centre National de la Recherche Scientifique, Paris (FR)

( * ) Notice: Subject to any disclaimer, the term of this patent is extended or adjusted under 35 U.S.C. 154(b) by 915 days.

(21) Appl. No.: 13/119,120

(22) PCT Filed: Sep. 15, 2009

(86) PCT No.: PCT/FR2009/001094
§ 371 (c)(1),
(2), (4) Date: May 26, 2011

(87) PCT Pub. No.: WO2010/031918
PCT Pub. Date: Mar. 25, 2010

(65) Prior Publication Data
US 2011/0225683 A1   Sep. 15, 2011

(30) Foreign Application Priority Data

Sep. 16, 2008  (FR) .................................... 08 05060

(51) Int. Cl.
*C12N 15/113* (2010.01)
*C12N 15/82* (2006.01)

(52) U.S. Cl.
CPC ......... *C12N 15/8289* (2013.01); *C12N 15/113* (2013.01)

(58) Field of Classification Search
None
See application file for complete search history.

(56) References Cited

U.S. PATENT DOCUMENTS 5,914,447 A * 6/1999 Araya et al. .................. 800/274

FOREIGN PATENT DOCUMENTS

WO    94/18334    8/1994
WO    96/00232    1/1996

OTHER PUBLICATIONS

Amarzguioui et al (Cellular and Molecular Life Sciences, 54, pp. 1175-1202, 1998).*
Lonsdale et al (Phil. Trans. R. Soc. Lond. B 319, pp. 149-163, 1988).*
Val et al (Nucleic Acids Research, 39(21), pp. 9262-9274, 2011).*
Fechter et al (CMLS, 58, pp. 1547-1561, 2001).*
Florentz et al (tRNA: Structure, Biosynthesis, and Function, 10: tRNA-like structures in plant viral RNAs, 1995).*
Dreher et al (Virus Res, 139(2), pp. 217-229, 2009).*
de Smit et al (Nucleic Acids Research, 30(19), pp. 4232-4240, 2002).*
Lewin et al (TRENDS in Molecular Medicine, 7(5), pp. 221-228, 2001).*
Khan (Clinica Chimica Acta, 367, pp. 20-27, 2006).*
Kubo et al (Mitochondrion, 8, pp. 5-14, 2008).*
Terasawa et al (Mol. Biol. Evol. 24(3), pp. 699-709, 2007).*
Dreher (Virus Research, 139, pp. 217-229, 2009, available online Jul. 30, 2008; May 20, 2014).*
Chase (Trends in Plant Science, 11(1), pp. 7-9, 2006).*
Val et al (P25, 6EME Rencontr. Sifrarn., 2006; see attached English translation).*
Val, P25 Manipulation de l'expression genetique dans les mitochondries de plante par l'import de sequences passageres associees a une structure de type ARNt, 6EME Rencontr Sifrarn, 2006.
Matsuda The tRNA-like Structure of Tunip Yellow Mosaic Virus RNA is a 3'-Translational Enhancer, Virology, 321, 36-46, 2004.
Siqueira, Marchantia Polymorpha Mitochondrial orf Identifies Transcribed Sequence in Angiosperm Mitochondrial Genome, Biochemica et Biophysica Acta 1520, 203-211, 2001.
Database EMBL, Arabidopsis Thaliana Clone D10 mRNA Sequence, Database Accession No: AY299283, 2003.
Bussiere, Development of an Efficient cis-trans-cis Ribozyme Cassette to Inactivate Plant Genes, Plant Biotechnology Journal, 1, 423-435, 2003.

* cited by examiner

*Primary Examiner* — Elizabeth McElwain
*Assistant Examiner* — Stephen Uyeno
(74) *Attorney, Agent, or Firm* — Morgan, Lewis & Bockius LLP

(57) ABSTRACT

The present invention relates to a polyribonucleotide including a hammerhead trans-ribozyme directed against a plant mitochondrial RNA and a structure in the form of tRNA that can be aminoacylated by valine, and to the use thereof in plants in particular for inducing cytoplasmic male sterility.

30 Claims, 10 Drawing Sheets

US 9,441,243 B2

Figure 1:
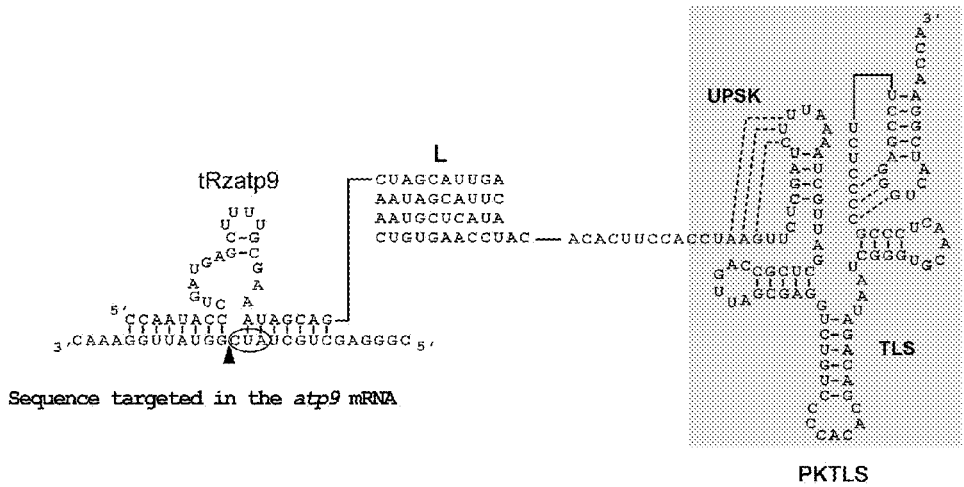

SEQUENCE LISTING

<160> NUMBER OF SEQ ID NOS: 69

<210> SEQ ID NO 1
<211> LENGTH: 278
<212> TYPE: DNA
<213> ORGANISM: artificial
<220> FEATURE:
<223> OTHER INFORMATION: Complete sequence of the gene construct used to express and import into mitochondria, in vivo, a trans-ribozyme
       directed against the atp9 mRNA
<220> FEATURE:
<221> NAME/KEY: misc_feature
<222> LOCATION: (1)..(33)
<223> OTHER INFORMATION: Sequence expressing the trans-ribozyme directed
       against the atp9 mRNA (tRzatp9)
<220> FEATURE:
<221> NAME/KEY: misc_feature
<222> LOCATION: (34)..(75)
<223> OTHER INFORMATION: Sequence expressing the linker sequence (L)
<220> FEATURE:
<221> NAME/KEY: misc_feature
<222> LOCATION: (76)..(195)
<223> OTHER INFORMATION: Sequence expressing the PKTLS sequence of TYMV
       (according to Matsuda and Dreher, 2004, Virology, 321, 36-46)
<220> FEATURE:
<221> NAME/KEY: misc_feature
<222> LOCATION: (196)..(278)
<223> OTHER INFORMATION: Sequence expressing the cis-ribozyme of HDV
       (cHDV) (according to Perrotta and Been, 1991, Nature, 350,
       434-436)

<400> SEQUENCE: 1 ccaatacccct gatgagcttt tgcgaaatag cagctagcat tgaaatagca ttcaatgctc      60
atactgtgaa cctacacact tccacctaag ttctcgatct ttaaaatcgt tagctcgcca     120
gttagcgagg tctgtcccca cacgacagat aatcgggtgc aactcccgcc cctcttccga     180
gggtcatcgg aaccagggtc ggcatggcat ctccacctcc tcgcggtccg acctgggcat     240
ccgaaggagg acgtcgtcca ctcggatggc taagggag                             278

<210> SEQ ID NO 2
<211> LENGTH: 195
<212> TYPE: RNA
<213> ORGANISM: artificial
<220> FEATURE:
<223> OTHER INFORMATION: Recombinant RNA
<220> FEATURE:
<221> NAME/KEY: misc_feature
<222> LOCATION: (1)..(33)
<223> OTHER INFORMATION: Trans-ribozyme directed against the atp9 mRNA
       (tRzatp9)
<220> FEATURE:
<221> NAME/KEY: misc_feature
<222> LOCATION: (34)..(75)
<223> OTHER INFORMATION: Linker sequence (L)
<220> FEATURE:
<221> NAME/KEY: misc_feature
<222> LOCATION: (76)..(195)
<223> OTHER INFORMATION: PKTLS sequence of TYMV (according to Matsuda
       and Dreher, 2004, Virology, 321, 36-46)

<400> SEQUENCE: 2
ccaauacccu gaugagcuuu ugcgaaauag cagcuagcau ugaaauagca uucaaugcuc      60
auacugugaa ccuacacacu uccaccuaag uucucgaucu uuaaaaucgu uagcucgcca     120
guuagcgagg ucuguccccca cacgacagau aaucggguce aacucccgcc cucuuccga     180 gggucaucgg aacca                                                      195

<210> SEQ ID NO 3
<211> LENGTH: 25
<212> TYPE: DNA
<213> ORGANISM: artificial
<220> FEATURE:
<223> OTHER INFORMATION: direct primer

<400> SEQUENCE: 3
catcggaacc agggtcggca tggca                                            25

```
<210> SEQ ID NO 4
<211> LENGTH: 23
<212> TYPE: DNA
<213> ORGANISM: artificial
<220> FEATURE:
<223> OTHER INFORMATION: reverse primer

<400> SEQUENCE: 4
ggtctctaga ctcccttagc cat                                              23

<210> SEQ ID NO 5
<211> LENGTH: 23
<212> TYPE: DNA
<213> ORGANISM: artificial
<220> FEATURE:
<223> OTHER INFORMATION: direct primer

<400> SEQUENCE: 5
gacggatccc ccgcatcgac ctg                                              23

<210> SEQ ID NO 6
<211> LENGTH: 293
<212> TYPE: RNA
<213> ORGANISM: Arabidopsis thaliana
<220> FEATURE:
<221> NAME/KEY: misc_feature
<222> LOCATION: (235)..(237)
<223> OTHER INFORMATION: triplet targeted by the tRzatp9 trans-ribozyme

<400> SEQUENCE: 6
uugucgagau ucaguugguc uucagucuac cacuccgugg guauaagauc gcaaagaaug       60
cauuccaagu gagaugucca agaucaaagg aacgagggua agaaucgacg aggaaucaau      120
aagauauaag auaagugaau gacaaagcgu gaguauaauu cucaacccga gauguuagaa      180
ggugcaaaau caauaggugc cggagcugcu acaauugcuu cagcgggagc ugcuaucggu      240
auuggaaacg uauucaguuc uuugauucau ucuguggcgc gaaauccauc auu            293

<210> SEQ ID NO 7
<211> LENGTH: 58
<212> TYPE: DNA
<213> ORGANISM: artificial
<220> FEATURE:
<223> OTHER INFORMATION: direct primer
<220> FEATURE:
<221> NAME/KEY: promoter
<222> LOCATION: (12)..(36)
<223> OTHER INFORMATION: phage T7 RNA polymerase promoter

<400> SEQUENCE: 7
agcaagaatt cgaattgtaa tacgactcac tataggttgt cgagattcag ttggtctt        58

<210> SEQ ID NO 8
<211> LENGTH: 32
<212> TYPE: DNA
<213> ORGANISM: artificial
<220> FEATURE:
<223> OTHER INFORMATION: reverse primer

<400> SEQUENCE: 8
gtacagaatt caatgatgga tttcgcgcca ca                                    32

<210> SEQ ID NO 9
<211> LENGTH: 85
<212> TYPE: DNA
<213> ORGANISM: artificial
```

```
<220> FEATURE:
<223> OTHER INFORMATION: primer

<400> SEQUENCE: 9
atgagctttt gcgaaatagc agctagcatt gaaatagcat tcaatgctca tactgtgaac      60
ctacacactt ccacctaagt tctcg                                            85

<210> SEQ ID NO 10
<211> LENGTH: 19
<212> TYPE: DNA
<213> ORGANISM: artificial
<220> FEATURE:
<223> OTHER INFORMATION: primer

<400> SEQUENCE: 10
tggttccgat gaccctcgg                                                   19

<210> SEQ ID NO 11
<211> LENGTH: 69
<212> TYPE: DNA
<213> ORGANISM: artificial
<220> FEATURE:
<223> OTHER INFORMATION: primer
<220> FEATURE:
<221> NAME/KEY: promoter
<222> LOCATION: (12)..(36)
<223> OTHER INFORMATION: T7 phage RNA polymerase promoter

<400> SEQUENCE: 11
agcaagaatt cgaattgtaa tacgactcac tataggccaa taccctgatg agcttttgcg      60
aaatagcag                                                              69

<210> SEQ ID NO 12
<211> LENGTH: 33
<212> TYPE: RNA
<213> ORGANISM: artificial
<220> FEATURE:
<223> OTHER INFORMATION: sequence encoding tRzatp9

<400> SEQUENCE: 12
ccaauacccu gaugagcuuu ugcgaaauag cag                                   33

<210> SEQ ID NO 13
<211> LENGTH: 107
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (45)..(86)
<223> OTHER INFORMATION: sequence encoding the linker sequence

<400> SEQUENCE: 13
gtacaaagct tccaataccc tgatgagctt ttgcgaaata gcagctagca ttgaaatagc      60
attcaatgct catactgtga acctacacac ttccacctaa gttctcg                   107

<210> SEQ ID NO 14
<211> LENGTH: 31
<212> TYPE: DNA
<213> ORGANISM: artificial
<220> FEATURE:
<223> OTHER INFORMATION: primer

<400> SEQUENCE: 14
```

```
agcaagaatt cctcccttag ccatccgagt g                                         31

<210> SEQ ID NO 15
<211> LENGTH: 20
<212> TYPE: DNA
<213> ORGANISM: artificial
<220> FEATURE:
<223> OTHER INFORMATION: primer

<400> SEQUENCE: 15
tggttccgat gaccctcgga                                                      20

<210> SEQ ID NO 16
<211> LENGTH: 22
<212> TYPE: DNA
<213> ORGANISM: artificial
<220> FEATURE:
<223> OTHER INFORMATION: primer

<400> SEQUENCE: 16
ccaataccct gatgagcttt tg                                                   22

<210> SEQ ID NO 17
<211> LENGTH: 20
<212> TYPE: DNA
<213> ORGANISM: artificial
<220> FEATURE:
<223> OTHER INFORMATION: primer

<400> SEQUENCE: 17
ctcccttagc catccgagtg                                                      20

<210> SEQ ID NO 18
<211> LENGTH: 46
<212> TYPE: DNA
<213> ORGANISM: artificial
<220> FEATURE:
<223> OTHER INFORMATION: direct primer

<400> SEQUENCE: 18
atgaattcga attgtaatac gactgactat agggcatttg gtctag                         46

<210> SEQ ID NO 19
<211> LENGTH: 24
<212> TYPE: DNA
<213> ORGANISM: artificial
<220> FEATURE:
<223> OTHER INFORMATION: reverse primer

<400> SEQUENCE: 19
caggatcctg gggggcattc cgag                                                 24

<210> SEQ ID NO 20
<211> LENGTH: 29
<212> TYPE: DNA
<213> ORGANISM: artificial
<220> FEATURE:
<223> OTHER INFORMATION: direct primer

<400> SEQUENCE: 20
gaattcggct aggtaacata atggaaatg                                            29

<210> SEQ ID NO 21
<211> LENGTH: 24
<212> TYPE: DNA
<213> ORGANISM: artificial
```

```
<220> FEATURE:
<223> OTHER INFORMATION: reverse primer

<400> SEQUENCE: 21
ggatccaggc caaggacggg gtcg                                              24

<210> SEQ ID NO 22
<211> LENGTH: 21
<212> TYPE: DNA
<213> ORGANISM: artificial
<220> FEATURE:
<223> OTHER INFORMATION: direct primer

<400> SEQUENCE: 22
acacttccac ctaagttctc g                                                 21

<210> SEQ ID NO 23
<211> LENGTH: 45
<212> TYPE: DNA
<213> ORGANISM: artificial
<220> FEATURE:
<223> OTHER INFORMATION: reverse primer
<220> FEATURE:
<221> NAME/KEY: promoter
<222> LOCATION: (1)..(26)
<223> OTHER INFORMATION: T7 phage RNA polymerase promoter

<400> SEQUENCE: 23
gaattgtaat acgactcact atagggtggt tccgatgacc ctcgg                       45

<210> SEQ ID NO 24
<211> LENGTH: 47
<212> TYPE: DNA
<213> ORGANISM: artificial
<220> FEATURE:
<223> OTHER INFORMATION: direct primer
<220> FEATURE:
<221> NAME/KEY: promoter
<222> LOCATION: (1)..(26)
<223> OTHER INFORMATION: T7 phage RNA polymerase promoter

<400> SEQUENCE: 24
gaattgtaat acgactcact atagggacac ttccacctaa gttctcg                     47

<210> SEQ ID NO 25
<211> LENGTH: 23
<212> TYPE: DNA
<213> ORGANISM: artificial
<220> FEATURE:
<223> OTHER INFORMATION: direct primer

<400> SEQUENCE: 25
catttggtct agtggtatga ttc                                               23

<210> SEQ ID NO 26
<211> LENGTH: 46
<212> TYPE: DNA
<213> ORGANISM: artificial
<220> FEATURE:
<223> OTHER INFORMATION: reverse primer
<220> FEATURE:
<221> NAME/KEY: promoter
<222> LOCATION: (1)..(26)
<223> OTHER INFORMATION: T7 phage RNA polymerase promoter

<400> SEQUENCE: 26
gaattgtaat acgactcact atagggtggg gggcattccg agaatc                      46
```

<210> SEQ ID NO 27
<211> LENGTH: 49
<212> TYPE: DNA
<213> ORGANISM: artificial
<220> FEATURE:
<223> OTHER INFORMATION: primer
<220> FEATURE:
<221> NAME/KEY: promoter
<222> LOCATION: (1)..(26)
<223> OTHER INFORMATION: T7 phage RNA polymerase promoter

<400> SEQUENCE: 27
gaattgtaat acgactcact atagggcatt tggtctagtg gtatgattc            49

<210> SEQ ID NO 28
<211> LENGTH: 20
<212> TYPE: DNA
<213> ORGANISM: artificial
<220> FEATURE:
<223> OTHER INFORMATION: reverse primer

<400> SEQUENCE: 28 tgggggcat tccgagaatc                                             20

<210> SEQ ID NO 29
<211> LENGTH: 21
<212> TYPE: DNA
<213> ORGANISM: artificial
<220> FEATURE:
<223> OTHER INFORMATION: primer

<400> SEQUENCE: 29
aggttcacgt atgagcattg a                                          21

<210> SEQ ID NO 30
<211> LENGTH: 27
<212> TYPE: DNA
<213> ORGANISM: artificial
<220> FEATURE:
<223> OTHER INFORMATION: primer

<400> SEQUENCE: 30
atgctatttc aatgctagct gctatttt                                   27

<210> SEQ ID NO 31
<211> LENGTH: 26
<212> TYPE: DNA
<213> ORGANISM: artificial
<220> FEATURE:
<223> OTHER INFORMATION: primer

<400> SEQUENCE: 31
atctttaaaa tcgttagctc gccagt                                     26

<210> SEQ ID NO 32
<211> LENGTH: 225
<212> TYPE: RNA
<213> ORGANISM: Nicotiana tabacum
<220> FEATURE:
<221> NAME/KEY: misc_feature
<222> LOCATION: (64)..(66)
<223> OTHER INFORMATION: target triplet of the tRzatp9-L-PKTLS RNA

<400> SEQUENCE: 32
auguuagaag gugcaaaauu aaugggugca ggagcugcua caauugcuuu agcgggagcu    60
gcuaucggua uuggaaacgu uuuuaguucu uugauucauu ccguggcgcg aaauccauca   120
uuggcaaaac aauuauuugg uuaugccauu uugggcuuug cucuaaccga agcuauugca    180
uuguuugccc uaaugauggc cuuuuugauc uuauucguau ucuaa                   225

<210> SEQ ID NO 33
<211> LENGTH: 23
<212> TYPE: DNA
<213> ORGANISM: artificial
<220> FEATURE:
<223> OTHER INFORMATION: primer

<400> SEQUENCE: 33
gcaaacgatg caatagcttc ggt                                            23

<210> SEQ ID NO 34
<211> LENGTH: 22
<212> TYPE: DNA
<213> ORGANISM: artificial
<220> FEATURE:
<223> OTHER INFORMATION: primer

<400> SEQUENCE: 34
tgctacaatt gcttcagcgg ga                                             22

<210> SEQ ID NO 35
<211> LENGTH: 23
<212> TYPE: DNA
<213> ORGANISM: artificial
<220> FEATURE:
<223> OTHER INFORMATION: direct primer

<400> SEQUENCE: 35
cgaagaattg catgaggaag ggc                                            23

<210> SEQ ID NO 36
<211> LENGTH: 21
<212> TYPE: DNA
<213> ORGANISM: artificial
<220> FEATURE:
<223> OTHER INFORMATION: primer

<400> SEQUENCE: 36
gccagtggcc gtacaacagg t                                              21

<210> SEQ ID NO 37
<211> LENGTH: 21
<212> TYPE: DNA
<213> ORGANISM: artificial
<220> FEATURE:
<223> OTHER INFORMATION: direct primer

<400> SEQUENCE: 37
cttgcccgct tccaattgat g                                              21

<210> SEQ ID NO 38
<211> LENGTH: 20
<212> TYPE: DNA
<213> ORGANISM: artificial
<220> FEATURE:
<223> OTHER INFORMATION: primer

<400> SEQUENCE: 38
ctgccaagcc gataggcgaa                                                20

<210> SEQ ID NO 39

```
<211> LENGTH: 27
<212> TYPE: DNA
<213> ORGANISM: artificial
<220> FEATURE:
<223> OTHER INFORMATION: primer

<400> SEQUENCE: 39
ctaacggact tagaatacga ataagat                                            27

<210> SEQ ID NO 40
<211> LENGTH: 193
<212> TYPE: RNA
<213> ORGANISM: artificial
<220> FEATURE:
<223> OTHER INFORMATION: Recombinant RNA
<220> FEATURE:
<221> NAME/KEY: misc_feature
<222> LOCATION: (1)..(33)
<223> OTHER INFORMATION: trans-ribozyme directed against the mnc1 RNA
      (tRzmnc1)
<220> FEATURE:
<221> NAME/KEY: misc_feature
<222> LOCATION: (34)..(73)
<223> OTHER INFORMATION: linker sequence (L)
<220> FEATURE:
<221> NAME/KEY: misc_feature
<222> LOCATION: (74)..(193)
<223> OTHER INFORMATION: PKTLS sequence of TYMV (according to Matsuda
      and Dreher, 2004, Virology, 321, 36-46)

<400> SEQUENCE: 40
aauccagccu gaugagcuuu ugcgaaacug gccacuugcc uauagcacaa ucuauucaug        60
aacaauagaa gauacacuuc caccuaaguu cucgaucuuu aaaaucguua gcucgccagu       120
uagcgagguc uguccccaca cgacagauaa ucgggugcaa cucccgcccc ucuuccgagg       180
gucaucggaa cca                                                         193

<210> SEQ ID NO 41
<211> LENGTH: 294
<212> TYPE: RNA
<213> ORGANISM: Arabidopsis thaliana
<220> FEATURE:
<221> NAME/KEY: misc_feature
<222> LOCATION: (236)..(238)
<223> OTHER INFORMATION: target triplet of the tRzmnc1 trans-ribozyme

<400> SEQUENCE: 41
ugcuuugcuc gcuccgacga uucuacauac cggccgaaag agacugagcc cgggcgaagc        60
caaucacauu gaguuguaga uugacauagu uaaccuucag ugcacuuaua uauaauauau       120
agucagaguu gaagcugagc guucaccuua gcggcaccuc ugaccucaga ugcauguguu       180
aagcauauaa cuagcgagcg aaccauacuu cggauaucgg cucggagcaa ggccagucgc       240
uggauuaaga cuaacaggac cauuccuuau gaaagaccca gcaagagacg ucac             294

<210> SEQ ID NO 42
<211> LENGTH: 54
<212> TYPE: DNA
<213> ORGANISM: artificial
<220> FEATURE:
<223> OTHER INFORMATION: direct primer
<220> FEATURE:
<221> NAME/KEY: promoter
<222> LOCATION: (12)..(36)
<223> OTHER INFORMATION: T7 phage RNA polymerase promoter

<400> SEQUENCE: 42
agcaagaatt cgaattgtaa tacgactcac tataggtgct ttgctcgctc cgac             54
```

<210> SEQ ID NO 43
<211> LENGTH: 29
<212> TYPE: DNA
<213> ORGANISM: artificial
<220> FEATURE:
<223> OTHER INFORMATION: primer

<400> SEQUENCE: 43
gtacagaatt cgtgacgtct cttgctggg                               29

<210> SEQ ID NO 44
<211> LENGTH: 81
<212> TYPE: DNA
<213> ORGANISM: artificial
<220> FEATURE:
<223> OTHER INFORMATION: primer

<400> SEQUENCE: 44
gagcttttgc gaaactggcc acttgcctat agcacaatct attcatgaac aatagaagat    60
acacttccac ctaagttctc g                                            81

<210> SEQ ID NO 45
<211> LENGTH: 69
<212> TYPE: DNA
<213> ORGANISM: artificial
<220> FEATURE:
<223> OTHER INFORMATION: primer
<220> FEATURE:
<221> NAME/KEY: promoter
<222> LOCATION: (12)..(36)
<223> OTHER INFORMATION: T7 phage RNA polymerase promoter

<400> SEQUENCE: 45
agcaagaatt cgaattgtaa tacgactcac tataggaatc cagcctgatg agcttttgcg    60
aaactggcc                                                          69

<210> SEQ ID NO 46
<211> LENGTH: 33
<212> TYPE: RNA
<213> ORGANISM: artificial
<220> FEATURE:
<223> OTHER INFORMATION: tRzmnc1 trans-ribozyme

<400> SEQUENCE: 46
aauccagccu gaugagcuuu ugcgaaacug gcc                                33

<210> SEQ ID NO 47
<211> LENGTH: 276
<212> TYPE: DNA
<213> ORGANISM: artificial
<220> FEATURE:
<223> OTHER INFORMATION: Complete sequence of the gene construct used to
      express and import into mitochondria, in vivo, a trans-ribozyme
      directed against the mnc1 mitochondrial RNA
<220> FEATURE:
<221> NAME/KEY: misc_feature
<222> LOCATION: (1)..(33)
<223> OTHER INFORMATION: sequence expressing the trans-ribozyme directed
      against mnc1 RNA (tRzmnc1)
<220> FEATURE:
<221> NAME/KEY: misc_feature
<222> LOCATION: (34)..(73)
<223> OTHER INFORMATION: sequence expressing the linker sequence (L)
<220> FEATURE:
<221> NAME/KEY: misc_feature
<222> LOCATION: (74)..(193)
<223> OTHER INFORMATION: sequence expressing the PKTLS sequence of TYMV

```
                    (according to Matsuda and Dreher, 2004, Virology, 321, 36-46)
<220> FEATURE:
<221> NAME/KEY: misc_feature
<222> LOCATION: (194)..(276)
<223> OTHER INFORMATION: sequence expressing the cis-ribozyme of HDV
      (cHDV) (according to Perrotta and Been, 1991, Nature, 350,
      434-436)

<400> SEQUENCE: 47
aatccagcct gatgagcttt tgcgaaactg gccacttgcc tatagcacaa tctattcatg      60
aacaatagaa gatacacttc cacctaagtt ctcgatcttt aaaatcgtta gctcgccagt     120
tagcgaggtc tgtccccaca cgacagataa tcgggtgcaa ctcccgcccc tcttccgagg     180
gtcatcggaa ccagggtcgg catggcatct ccacctcctc gcggtccgac ctgggcatcc     240
gaaggaggac gtcgtccact cggatggcta agggag                              276

<210> SEQ ID NO 48
<211> LENGTH: 105
<212> TYPE: DNA
<213> ORGANISM: artificial
<220> FEATURE:
<223> OTHER INFORMATION: direct primer

<400> SEQUENCE: 48
gtacaaagct taatccagcc tgatgagctt ttgcgaaact ggccacttgc ctatagcaca      60
atctattcat gaacaataga agatacactt ccacctaagt tctcg                    105

<210> SEQ ID NO 49
<211> LENGTH: 193
<212> TYPE: RNA
<213> ORGANISM: artificial
<220> FEATURE:
<223> OTHER INFORMATION: Recombinant RNA
<220> FEATURE:
<221> NAME/KEY: misc_feature
<222> LOCATION: (1)..(33)
<223> OTHER INFORMATION: trans-ribozyme directed against the or78 RNA
      (tRzor78)
<220> FEATURE:
<221> NAME/KEY: misc_feature
<222> LOCATION: (34)..(73)
<223> OTHER INFORMATION: linker sequence (L)
<220> FEATURE:
<221> NAME/KEY: misc_feature
<222> LOCATION: (74)..(193)
<223> OTHER INFORMATION: PKTLS sequence of TYMV (according to Matsuda
      and Dreher, 2004, Virology, 321, 36-46)

<400> SEQUENCE: 49
ccuauguccu gaugagcuuu ugcgaaacgu ugugaccagc agcugccagu aacacaccua      60
cgugcgcugc caaacacuuc caccuaaguu cucgaucuuu aaaaucguua gcucgccagu     120
uagcgagguc uguccccaca cgacagauaa ucggguugcaa cucccgcccc ucuuccgagg    180
gucaucggaa cca                                                       193

<210> SEQ ID NO 50
<211> LENGTH: 504
<212> TYPE: RNA
<213> ORGANISM: Solanum tuberosum
<220> FEATURE:
<221> NAME/KEY: misc_feature
<222> LOCATION: (89)..(91)
<223> OTHER INFORMATION: target triplet of the tRzor78 trans-ribozyme

<400> SEQUENCE: 50
ggccgaucuc aagcuggaug agaaggcaaa ccaaccccucc gaagaaggaa acuaugacua     60
```

```
auuagaccgu uagugaccaa augacaacgu cgacauagga aaagaaggug agauagggga    120
uggaagcagg guagugcuaa cucugcauca cgcggcuauu uuggcucuuu ccggagagca    180
ucaaaucaac cgcuuucauu ugcuuugaga cugacccucu ccaggcgaa aaggggaagg     240 agcuuuccaa ucgaucacac gcccggcaca agagaaggaa gggcaagaga auaaauaggc    300
acuggcauau ugacuacuug aaauacggac uauauaagaa aaaugggag ggaaugagaa     360 gaaagccuau uugcaggcaa caaggauuug cugcuuucuu aguuagaaaa aggaguuacc    420
uagcuagugg agcgagguag uuuacuugcc uuuccacgau uccuacauug agcucucugu    480
gccuuacuua uuaugaguug auaa                                          504
```

```
<210> SEQ ID NO 51
<211> LENGTH: 54
<212> TYPE: DNA
<213> ORGANISM: artificial
<220> FEATURE:
<223> OTHER INFORMATION: direct primer
<220> FEATURE:
<221> NAME/KEY: promoter
<222> LOCATION: (12)..(36)
<223> OTHER INFORMATION: T7 phage RNA polymerase promoter

<400> SEQUENCE: 51
agcaagaatt cgaattgtaa tacgactcac tataggccga tctcaagctg gatg         54

<210> SEQ ID NO 52
<211> LENGTH: 35
<212> TYPE: DNA
<213> ORGANISM: artificial
<220> FEATURE:
<223> OTHER INFORMATION: reverse primer

<400> SEQUENCE: 52
gtacagaatt cttatcaact cataataagt aaggc                              35

<210> SEQ ID NO 53
<211> LENGTH: 83
<212> TYPE: DNA
<213> ORGANISM: artificial
<220> FEATURE:
<223> OTHER INFORMATION: primer

<400> SEQUENCE: 53
atgagctttt gcgaaacgtt gtgaccagca gctgccagta acacacctac gtgcgctgcc    60
aaacacttcc acctaagttc tcg                                           83

<210> SEQ ID NO 54
<211> LENGTH: 69
<212> TYPE: DNA
<213> ORGANISM: artificial
<220> FEATURE:
<223> OTHER INFORMATION: primer
<220> FEATURE:
<221> NAME/KEY: promoter
<222> LOCATION: (12)..(36)
<223> OTHER INFORMATION: T7 phage RNA polymerase promoter

<400> SEQUENCE: 54
agcaagaatt cgaattgtaa tacgactcac tataggccta tgtcctgatg agcttttgcg    60
aaacgttgt                                                           69

<210> SEQ ID NO 55
```

```
<211> LENGTH: 33
<212> TYPE: RNA
<213> ORGANISM: artificial
<220> FEATURE:
<223> OTHER INFORMATION: tRzor78 trans-ribozyme

<400> SEQUENCE: 55
ccuauguccu gaugagcuuu ugcgaaacgu ugu                            33

<210> SEQ ID NO 56
<211> LENGTH: 276
<212> TYPE: DNA
<213> ORGANISM: artificial
<220> FEATURE:
<223> OTHER INFORMATION: Complete sequence of the gene construct used to
      express and import into mitochondria, in vivo, a trans-ribozyme
      directed against the or78 mitochondrial RNA
<220> FEATURE:
<221> NAME/KEY: misc_feature
<222> LOCATION: (1)..(33)
<223> OTHER INFORMATION: sequence expressing the trans-ribozyme directed
      against the or78 RNA (tRzor78)
<220> FEATURE:
<221> NAME/KEY: misc_feature
<222> LOCATION: (34)..(73)
<223> OTHER INFORMATION: sequence expressing the linker sequence (L)
<220> FEATURE:
<221> NAME/KEY: misc_feature
<222> LOCATION: (74)..(193)
<223> OTHER INFORMATION: sequence expressing the PKTLS sequence of TYMV
      (according to Matsuda and Dreher, 2004, Virology, 321, 36-46)
<220> FEATURE:
<221> NAME/KEY: misc_feature
<222> LOCATION: (194)..(276)
<223> OTHER INFORMATION: sequence expressing the cis-ribozyme of HDV
      (cHDV) (according to Perrotta and Been, 1991, Nature, 350,
      434-436)

<400> SEQUENCE: 56
cctatgtcct gatgagcttt tgcgaaacgt tgtgaccagc agctgccagt aacacaccta    60
cgtgcgctgc caaacacttc cacctaagtt ctcgatcttt aaaatcgtta gctcgccagt   120
tagcgaggtc tgtccccaca cgacagataa tcgggtgcaa ctcccgcccc tcttccgagg   180
gtcatcggaa ccagggtcgg catggcatct ccacctcctc gcggtccgac ctgggcatcc   240
gaaggaggac gtcgtccact cggatggcta agggag                            276

<210> SEQ ID NO 57
<211> LENGTH: 105
<212> TYPE: DNA
<213> ORGANISM: artificial
<220> FEATURE:
<223> OTHER INFORMATION: direct primer

<400> SEQUENCE: 57
gtacaaagct tcctatgtcc tgatgagctt ttgcgaaacg ttgtgaccag cagctgccag    60
taacacacct acgtgcgctg ccaaacactt ccacctaagt tctcg                   105

<210> SEQ ID NO 58
<211> LENGTH: 213
<212> TYPE: RNA
<213> ORGANISM: artificial
<220> FEATURE:
<223> OTHER INFORMATION: Recombinant RNA
<220> FEATURE:
<221> NAME/KEY: misc_feature
<222> LOCATION: (1)..(53)
<223> OTHER INFORMATION: trans-ribozyme directed against the or78 RNA
      (tRzor78TS)
<220> FEATURE:
```

```
<221> NAME/KEY: misc_feature
<222> LOCATION: (54)..(93)
<223> OTHER INFORMATION: Linker sequence (L)
<220> FEATURE:
<221> NAME/KEY: misc_feature
<222> LOCATION: (94)..(213)
<223> OTHER INFORMATION: PKTLS sequence of TYMV (according to Matsuda
      and Dreher, 2004, Virology, 321, 36-46)

<400> SEQUENCE: 58
gcuaaggcaa acgcuaugcu auguccugau gagucggaaa cgacgaaacg uugacuugcc      60
uauagcacaa ucuauucaug aacaauagaa gauacacuuc caccuaaguu cucgaucuuu     120
aaaaucguua gcucgccagu uagcgagguc ugucccccaca cgacagauaa ucgggugcaa    180
cucccgcccc ucuuccgagg gucaucggaa cca                                  213

<210> SEQ ID NO 59
<211> LENGTH: 191
<212> TYPE: RNA
<213> ORGANISM: artificial
<220> FEATURE:
<223> OTHER INFORMATION: Recombinant RNA
<220> FEATURE:
<221> NAME/KEY: misc_feature
<222> LOCATION: (2)..(31)
<223> OTHER INFORMATION: trans-ribozyme directed against the or78 RNA
      (tRzor78/6+6)
<220> FEATURE:
<221> NAME/KEY: misc_feature
<222> LOCATION: (32)..(71)
<223> OTHER INFORMATION: linker sequence (L)
<220> FEATURE:
<221> NAME/KEY: misc_feature
<222> LOCATION: (72)..(191)
<223> OTHER INFORMATION: PKTLS sequence of TYMV (according to Matsuda
      and Dreher, 2004, Virology, 321, 36-46)

<400> SEQUENCE: 59
guauguccug augagcuuuu gcgaaacguu ggagaagaag cugccaguaa cacaccuacg      60
ugcgcugcca aacacuucca ccuaaguucu cgaucuuuaa aaucguuagc ucgccaguua    120
gcgaggucug uccccacacg acagauaauc gggugcaacu cccgcccuc uuccgagggu     180 caucggaacc a                                                         191

<210> SEQ ID NO 60
<211> LENGTH: 216
<212> TYPE: RNA
<213> ORGANISM: artificial
<220> FEATURE:
<223> OTHER INFORMATION: Recombinant RNA
<220> FEATURE:
<221> NAME/KEY: misc_feature
<222> LOCATION: (1)..(56)
<223> OTHER INFORMATION: trans-ribozyme directed against the or78 RNA
      (tRzor78TS/8+7)
<220> FEATURE:
<221> NAME/KEY: misc_feature
<222> LOCATION: (57)..(96)
<223> OTHER INFORMATION: linker sequence (L)
<220> FEATURE:
<221> NAME/KEY: misc_feature
<222> LOCATION: (97)..(216)
<223> OTHER INFORMATION: PKTLS sequence of TYMV (according to Matsuda
      and Dreher, 2004, Virology, 321, 36-46)

<400> SEQUENCE: 60
gcuaaggcaa acgcuaugcc cuauguccug augagucgga aacgacgaaa cguugacuu      60 gaauauagca caaucuauuc augaacaaaa gaagauacac uuccaccuaa guucucgauc    120
```
uuuaaaaucg uuagcucgcc aguuagcgag gucugucccc acacgacaga uaaucgggug       180
caacucccgc cccucuuccg agggucaucg gaacca                               216

<210> SEQ ID NO 61
<211> LENGTH: 82
<212> TYPE: DNA
<213> ORGANISM: artificial
<220> FEATURE:
<223> OTHER INFORMATION: direct primer

<400> SEQUENCE: 61
gtcggaaacg acgaaacgtt gacttgccta tagcacaatc tattcatgaa caatagaaga      60
tacacttcca cctaagttct cg                                              82

<210> SEQ ID NO 62
<211> LENGTH: 88
<212> TYPE: DNA
<213> ORGANISM: artificial
<220> FEATURE:
<223> OTHER INFORMATION: direct primer

<400> SEQUENCE: 62
agcaagaatt cgaattgtaa tacgactcac tataggctaa ggcaaacgct atgctatgtc     60
ctgatgagtc ggaaacgacg aaacgttg                                        88

<210> SEQ ID NO 63
<211> LENGTH: 83
<212> TYPE: DNA
<213> ORGANISM: artificial
<220> FEATURE:
<223> OTHER INFORMATION: direct primer

<400> SEQUENCE: 63
gatgagcttt tgcgaaacgt tggagaagaa gctgccagta acacacctac gtgcgctgcc     60
aaacacttcc acctaagttc tcg                                             83

<210> SEQ ID NO 64
<211> LENGTH: 66
<212> TYPE: DNA
<213> ORGANISM: artificial
<220> FEATURE:
<223> OTHER INFORMATION: direct primer

<400> SEQUENCE: 64
agcaagaatt cgaattgtaa tacgactcac tataggtatg tcctgatgag cttttgcgaa     60
acgttg                                                                66

<210> SEQ ID NO 65
<211> LENGTH: 82
<212> TYPE: DNA
<213> ORGANISM: artificial
<220> FEATURE:
<223> OTHER INFORMATION: direct primer

```
<400> SEQUENCE: 65
tcggaaacga cgaaacgttg tacttgaata tagcacaatc tattcatgaa caaaagaaga      60
tacacttcca cctaagttct cg                                               82

<210> SEQ ID NO 66
<211> LENGTH: 91
<212> TYPE: DNA
<213> ORGANISM: artificial
<220> FEATURE:
<223> OTHER INFORMATION: direct primer

<400> SEQUENCE: 66
agcaagaatt cgaattgtaa tacgactcac tataggctaa ggcaaacgct atgccctatg      60
tcctgatgag tcggaaacga cgaaacgttg t                                     91

<210> SEQ ID NO 67
<211> LENGTH: 210
<212> TYPE: DNA
<213> ORGANISM: artificial
<220> FEATURE:
<223> OTHER INFORMATION: cloned CR-RT-PCR products

<400> SEQUENCE: 67
tcactagtca ttatctttaa aatcgttagc tcgccagtta gcgaggtctg tccccacacg      60
acagataatc gggtgcaact cccgcccctc ttccgagggt catcggaacc aacgctgaag     120
ctagtcgact ctagcctcga ggcgcgccaa gcttccaata ccctgatgag cttttgcgaa     180
atagcagcta gcattgaaat agcataatcg                                      210

<210> SEQ ID NO 68
<211> LENGTH: 210
<212> TYPE: DNA
<213> ORGANISM: artificial
<220> FEATURE:
<223> OTHER INFORMATION: sequence of the excepted result

<400> SEQUENCE: 68
tcactagtca ttatctttaa aatcgttagc tcgccagtta gcgaggtctg tccccacacg      60
acagataatc gggtgcaact cccgcccctc ttccgagggt catcggaacc aacgctgaag     120
ctagtcgact ctagcctcga ggcgcgccaa gcttccaata ccctgatgag cttttgcgaa     180
atagcagcta gcattgaaat agcataatcg                                      210

<210> SEQ ID NO 69
<211> LENGTH: 193
<212> TYPE: DNA
<213> ORGANISM: artificial
<220> FEATURE:
<223> OTHER INFORMATION: key overlapping sequence

<400> SEQUENCE: 69
atctttaaaa tcgttagctc gccagttagc gaggtctgtc cccacacgac agataatcgg      60
gtgcaactcc cgcccctctt ccagggtca tcggaaccaa cgctgaagct agtcgactct     120
agcctcgagg cgcgccaagc ttccaatacc ctgatgagct tttgcgaaat agcagctagc     180
attgaaatag cat                                                        193
```

IMPORTATION OF A RIBOZYME INTO VEGETABLE MITOCHONDRIA BY A PSEUDO-TRNA THAT CAN BE AMINOACYLATED BY VALINE

RELATED APPLICATIONS

The present application is a U.S. National Phase Application of International Application No. PCT/FR2009/001094 (filed Sep. 15, 2009) which claims priority to French Application No. 0805060 (filed Sep. 16, 2008) which are hereby incorporated by reference in their entirety.

SEQUENCE LISTING SUBMISSION VIA EFS-Web

A computer readable text file, entitled "045636-5166_SequenceListing.txt," created on or about Mar. 15, 2011, with a file size of about 22 kb contains the sequence listing for this application and is hereby incorporated by reference in its entirety.

The present invention relates to novel means for importing a ribozyme into plant mitochondria, and more particularly for obtaining plants having a cytoplasmic male sterility.

The obtaining of novel plant varieties is a process which takes place in several steps over many years. Whether for allogamous plants or autogamous plants, varietal selection involves crossing between two homozygous parental genotypes A and B having advantageous agronomic characteristics (for example, disease resistance, parasite resistance, yield, etc.). In order to homogenize the crosses and to facilitate selection, it is necessary to cross a sterile male parent A (i.e. one which does not produce anthers or functional pollen) with a fertile parent B. Thus, a set of male-sterile plants originating from the same parental variety A is crossed with numerous different parental varieties B, in order to search for the best genetic combinations. Varietal selection will be carried out on the F1 hybrids thus obtained from the various crosses.

However, most plant species of agronomic interest are capable of self-pollinating, but few plant lines are naturally male-sterile. It is therefore necessary to generate this property. Male-sterile plants of a line A can be obtained in two conventional ways.

The first, and the simplest, consists in castrating the plants. For example, for corn, this castration is tedious and expensive since it requires a very large number of individuals. Castration using machines can also be carried out, but it is often less effective. In the case of wheat, castration is chemical but can lead to losses in seed production yield, thus reducing the possibility of selection. In addition, the gametocides used often have phytotoxic effects and are often dangerous to human health.

The second technique consists in causing cytoplasmic male sterility (CMS) in order to obtain a genetically male-sterile line A. However, the obtaining of such varieties by crossing methods requires many years of investigation and selection. This is because, in order to "convert" a male-fertile line of interest into a male-sterile line A, it is necessary, firstly, to cross it with a line C which does not have any particularly advantageous characteristics, but which is naturally male-sterile. The chromosomal background of the line C is eliminated by a series of backcrosses (6 in general, at a rate of 6 months to 1 year per backcross), thus making it possible to obtain a male-sterile line A. It is this line which will be crossed with the line B of which the characteristics are advantageous.

In addition, these various techniques for obtaining male-sterile lines are highly dependent on the plant species under consideration and, at the current time, no methodology exists which is applicable to all the plants of agronomic interest cultivated.

Some genetic engineering methods for inducing male sterility in plants are, moreover, known.

One of these methods uses the gene encoding the BARNASE ribonuclease of *Bacillus amyloliquefaciens* (see international application WO 96/026283 and patent application EP 1 020 527). The gene encoding BARNASE can be placed under the control of a promoter for specific expression in the pollen, and then introduced into the nuclear genome of the plant cells by genetic transformation. The expression of BARNASE then brings about destruction of the RNA in the pollen grains that are in the process of forming, leading to degeneration thereof. The term used here is nuclear male sterility since the transgene is inserted into the nucleus of the transformed plant cell and the phenomenon which ensues therefrom does not involve the organelles.

It is also known that the importation into the mitochondria of a protein expressed by an unedited coding sequence of a higher-plant mitochondrial gene (for example, the gene encoding the wheat ATP9 protein), by means of a polypeptide capable of importing a protein into the mitochondria, makes it possible to obtain male-sterile plants (international application WO 94/018334; Hernould et al., 1993, *P.N.A.S. USA*, 90, 2370-2374). However, the mitochondria of these plants have the drawback of comprising both proteins that are naturally expressed by the mitochondria and proteins expressed by the unedited coding sequence inserted into the nuclear genome, thus reducing the effectiveness of this technique.

Moreover, the knockdown of a mitochondrial RNA of plant cells, such as the atp9 mRNA or a noncoding regulatory RNA, could make it possible to obtain plants having cytoplasmic male sterility (CMS). Thus, for example, in *Brassica napus*, there is a single gene in the mitochondrial genome encoding the ATP9 protein. A male-sterile variety, called *B. napus* CMS "Tournefortii-Stiewe" and resulting from a fusion of protoplasts between *B. napus* and *B. tournefortii*, has been obtained. This variety has three atp9 genes (atp9-1a, atp9-1b and atp9-2). A sequence called orf193 has been found upstream of atp9-2. orf193 is cotranscribed with atp9-2. No stop codon exists between orf193 and atp9-2, suggesting the production of a new protein that can compete with the ATP9 protein in the assembly of the ATP-synthase complex (Dieterich et al., 2003, *Mol Genet Genomics*, 269, 723-731). In addition, in the sunflower, a line, CMS-PEP1, has been isolated and it has been noted that it has an additional fragment of 500 nucleotides in the 3'UTR region of the atp9 gene. This additional sequence appears to be responsible for the cytoplasmic male sterility present in this line (De La Canal, 2001, *Theor Appl Genet*, 102, 1185-1189). Moreover, in chive, the cytoplasmic male sterility on the CMS1 line is due to the presence of an additional sequence of 762 base pairs in the 3' region of the coding portion of the atp9 gene (Engelke et al., 2002, *Theor Appl Genet*, 104, 698-702).

Plant cell mitochondria have a principal genome of approximately 220 to 740 kilobases, but which has a low gene density, and also, very often, plasmids independent of the principal genome. Mitochondria are the seat of complex genetic mechanisms. Genomic, transcriptomic and proteomic approaches over the past few years have provided a great deal of information on the role and function of mitochondria. However, the investigations remain limited by the lack of tools enabling the transformation of mitochondria in plant cells and the manipulation of mitochondrial genetic expression. Furthermore, the absence of reverse genetics approaches, and more particularly the absence of data suggesting mitochondrial targeting of a system of DICER/RISC type or the existence in the organelles of enzymes that have equivalent activities, makes it difficult to identify new genes and new regulatory functions in the vast unassigned regions of plant mitochondrial genomes.

During previous studies, the inventors showed that the TLS ("tRNA-like structure") sequence, that can be amino-acylated by valine, of the TYMV virus (turnip yellow mosaic virus, GI accession number 62218 in the Genbank database) could serve as a vector for the importation of a passenger RNA sequence, consisting of the 104 nucleotides naturally located upstream of the TLS sequence, into the TYMV genome. They express, in a plant cell, after genetic transformation, a composite (recombinant) RNA sequence comprising said passenger RNA sequence combined with said TLS sequence, the TLS sequence being itself combined, at its 3' end, with the sequence of the cis-ribozyme of HDV (Hepatitis Delta virus). The function of the HDV ribozyme is to free the 3' end of the TLS sequence after transcription, thus generating the TLS sequence combined, at its 5' end, with the passenger RNA sequence.

The inventors have now envisioned a novel approach for manipulating genetic expression in plant cell mitochondria by developing an antisense strategy based on a ribozyme.

The inventors have investigated whether replacing the nonfunctional sequence of 104 nucleotides, described above, with a functional sequence of complex structure, such as a trans-ribozyme, makes it possible to preserve, firstly, the importation functionalities of the TLS sequence and, secondly, the catalytic functionalities of the ribozyme.

For this purpose, the inventors have prepared a genetic construct (polyribonucleotide) combining the sequence of a hammerhead ribozyme targeting a mitochondrial RNA, with the PKTLS sequence, that can be aminoacylated by valine, of TYMV (Matsuda and Dreher, 2004, Virology, 321, 36-46) and have noted that the construct can be imported into plant cell mitochondria and that, in addition, the ribozyme is functional, i.e. it is capable of specifically cleaving its target RNA in the mitochrondrion.

Hammerhead ribozymes are definitely those which are the most well-characterized of all the known natural ribozymes. They were initially discovered in viroids and satellite RNAs of viruses; cis-cleavage of hammerhead ribozymes allows maturation of the transcripts generated by rolling circle replication. The study of in-cis self-cleaving hammerhead ribozymes made it possible to define a consensus structure made up of 3 helices and a conserved core (De La Peña and Flores, 2001, J Biol Chem, 276, 34586-34593; Hammann and Lilley, 2002, Chembiochem, 3, 690-700) for the development of in-trans ribozyme/target systems (trans-ribozymes). This canonic structure was for a long time considered to be optimal. It was subsequently demonstrated that additional tertiary stabilizing motifs (TSMs) were essential for in vivo cleavage (De La Peña et al., 2003, EMBO J, 22, 5561-5570; Khvorova et al., 2003, Nat Struct Biol, 10, 708-712). It is this type of hammerhead ribozyme, stabilized by tertiary interactions ("tertiary stabilized hammerhead" or tsHH) which is currently considered to have the best effectiveness in vivo, in particular under conditions of low $Mg^{2+}$ concentration (Burke and Greathouse, 2005, BMC Biochem, 6, 14; Hoogstraten and Sumita, 2007, Biopolymers, 87, 317-328).

The inventors have also shown, surprisingly, that in the construct described above, the trans hammerhead ribozymes of approximately 30 to 34 nucleotides, without a tertiary stabilizing motif, and having in their stem-loop II, a loop consisting of 4 nucleotides (UUUU) and a helix II consisting of only 2 nucleotide pairs (G-C and C-G, from the 5' position to the 3' position), exhibit better target-RNA cleavage effectiveness than the tertiary stabilized (tsHH) trans hammerhead ribozymes, and having, in their stem-loop II, a loop consisting of 4 nucleotides (GAAA) and a helix II consisting of 4 nucleotide pairs (G-C, U-A, C-G, G-C, from the 5' position to the 3' position).

Consequently, a subject of the present invention is a polyribonucleotide (RNA) comprising, from its 5' end to its 3' end, a trans hammerhead ribozyme directed against a plant mitochondrial RNA and a tRNA-like structure that can be aminoacylated by valine.

The expression "tRNA-like structure that can be aminoacylated by valine" is intended to mean the RNA sequence mimicking a tRNA (tRNA-like structure, TLS), located in the 3' position of the genome of certain plant viruses, capable of being aminoacylated by valyl-tRNA synthetase and therefore of covalently bonding a valine residue in the 3' position. This structure is known as the $TLS^{val}$ sequence. The tRNA-like structure that can be aminoacylated by valine also bonds ATP(CTP):tRNA nucleotidyltransferase. $TLS^{val}$ in its valylated form is also capable of forming a complex with the EF-1A.GTP elongation factor. In addition, it is not generally recognized by RNase P in vivo. Those skilled in the art know several $TLS^{val}$ sequences (see, for example, Dreher, 2009, Virus Research, 139, 217-229). By way of nonlimiting example of tRNA-like structures that can be aminoacylated by valine, mention may be made of those contained in the genome of viruses belonging to the genera:

Tymovirus, more particularly to the Turnip yellow mosaic virus (TYMV), Andean potato latent virus (APLV), Belladonna mottle virus (BeMV), Cacao yellow mosaic virus (CYMV), Clitoria yellow vein virus (CYVV), Eggplant mosaic virus (EMV), Kennedya yellow mosaic virus (KYMV), Okra mosaic virus (OkMV), Ononis yellow mosaic virus (OYMV) and Wild cucumber mosaic virus (WCMV), Furovirus, more particularly to the Soil-borne wheat mosaic virus (SBWMV), Pomovirus, more particularly to the Beet soil-borne virus (BSBV) and Potato mop-top virus (PMTV), Pecluvirus, more particularly to the Indian peanut clump virus (IPCV) and Tobamovirus, more particularly to the Sunn-hemp mosaic virus (SHMV).

Preferably, said tRNA-like structure that can be aminoacylated by valine is that which is contained in the genome of a virus, preferably of a Tymovirus, and more preferably that which is contained in the genome of the Turnip yellow mosaic virus (Matsuda and Dreher, 2004, Virology, 321, 36-46 and Dreher, 2009, mentioned above).

Optionally, the last nucleotide located in the 3' position of said tRNA-like structure that can be aminoacylated by valine is an adenine (A). In the case where the $TLS^{val}$ sequence would not recognize the ATP(CTP):tRNA nucleotidyltransferase (allowing the addition of an adenine at its 3' end), for example when it is used in vitro, the addition of this adenine, so as to obtain at the 3' end of the $TLS^{val}$ sequence the triplet-CCA (cytosine-cytosine-adenine), is essential for the aminoacylation.

The term "ribozyme" is intended to mean a catalytic RNA molecule capable of specifically cleaving a target RNA sequence in cis or in trans (for review, see James and Gibson, 1998, *Blood,* 91, 371-382; Scott, 2007, *Curr Opin Chem Biol,* 11, 636-643). The ribozyme may be natural or artificially created (synthetic), in particular for targeting a target mitochondrial RNA.

The expression "trans-ribozyme directed against a plant mitochondrial RNA" is intended to mean a ribozyme capable of recognizing a target sequence contained in said mitochondrial RNA and of cleaving this mitochondrial RNA.

The target mitochondrial RNA can be any RNA expressed in plant mitochondria, in particular a messenger RNA (mRNA) or a noncoding RNA (ncRNA).

A trans hammerhead ribozyme is an RNA capable of cleaving a target RNA, other than itself. Trans hammerhead ribozymes are well known to those skilled in the art (Hammann and Lilley, 2002, *Chembiochem,* 3, 690-700; Persson et al., 2002, *Chembiochem,* 3, 1066-1071; Peracchi, 2004, *Rev. Med. Virol.,* 14, 47-64; Citti and Rainaldi, 2005, *Curr. Gene Ther.,* 5, 11-24). The trans hammerhead ribozyme/ substrate complex generally consists of an intramolecular helix (helix II) and two intermolecular helices (helices I and III).

According to one preferred embodiment of the invention, said trans hammerhead ribozyme consists of from 24 to 100 nucleotides, preferably from 30 to 40 nucleotides, and more preferably from 30 to 35 nucleotides.

According to another preferred embodiment of the invention, said trans hammerhead ribozyme has, in its stem-loop II, a loop consisting of 4 nucleotides (chosen from adenosine (A), cytidine (C), guanosine (G) and uridine (U)), which may be identical or different, preferably 4 uridines (UUUU), and a helix II consisting of 2 nucleotide pairs, preferably G-C and C-G.

According to one advantageous embodiment of the invention, said trans hammerhead ribozyme is of RzGII type with reference to the article by Persson et al., 2002 (mentioned above), i.e. it has, in its stem-loop II, a loop consisting of 4 uridines (UUUU), and a helix II consisting of 2 nucleotide pairs, G-C and C-G.

According to another preferred embodiment of the invention, said trans hammerhead ribozyme hybridizes to the target mitochondrial RNA (the substrate for the trans-ribozyme) by means of from 3 to 50 contiguous nucleotides, preferably from 5 to 10 contiguous nucleotides, more preferably 8 contiguous nucleotides, in the 5' position of said trans-ribozyme (corresponding to helix I of the trans-ribozyme hybridized to its target nucleotide sequence) and by means of from 30 to 50 contiguous nucleotides, preferably from 5 to 10 contiguous nucleotides, preferably 7 contiguous nucleotides, in the 3' position of said trans-ribozyme (corresponding to helix III of the trans-ribozyme hybridized to its target nucleotide sequence).

According to one advantageous embodiment of the invention, said trans-ribozyme and said tRNA-like structure that can be aminoacylated by valine are separated by a linker RNA sequence (L).

The term "linker RNA sequence" is intended to mean an RNA sequence, of approximately 40 nucleotides, preferably from 35 to 45 nucleotides, selected so as to avoid any intramolecular pairing (or any intramolecular hybridization) between said trans-ribozyme and the rest of said polyribonucleotide, in particular the TLS$^{val}$ or PKTLS sequences (see above). Thus, the function of the linker RNA sequence is to reduce or avoid the formation of alternative secondary structures within said polyribonucleotide, in particular between said trans-ribozyme and the TLS$^{val}$ or PKTLS sequences. It also makes it possible to move said trans-ribozyme away from the TLS$^{val}$ or PKTLS sequences, in order to avoid interference or a steric hindrance effect that would be detrimental to the functionality (would inhibit or reduce the function) of these various components. The linker RNA sequence also must not itself form secondary structures resulting in steric hindrance that would be detrimental to the functionality of said trans-ribozyme or of the TLS$^{val}$ or PKTLS sequences. Those skilled in the art can easily construct a linker RNA sequence as defined above using a secondary structure prediction software. By way of nonlimiting example of software, those skilled in the art can use the MFOLD software (Zuker, 1989, *Science* 244, 48-52; Zuker, 2003, *Nucleic Acids Res.* 31, 3406-3415 and Mathews et al., 1999, *J. Mol. Biol.* 288, 911-940).

According to another advantageous embodiment of the invention, said trans-ribozyme or said linker RNA sequence if it is present, and said tRNA-like structure that can be aminoacylated by valine, are separated by an upstream pseudoknot (UPSK). This upstream pseudoknot makes it possible to optimize the interaction of the tRNA-like structure that can be aminoacylated by valine, with the aminoacyl-tRNA synthetase.

By way of nonlimiting examples of upstream pseudoknots that can be used in the context of the present invention, mention may be made of those naturally located in the position 5' of a TLS sequence, preferably of a TLS$^{val}$ sequence, contained in the genome of a virus, preferably belonging to the Tymovirus, Furovirus, Pomovirus, Pecluvirus or Tobamovirus genus as defined above.

More preferably, said upstream pseudoknot is that which is contained in the genome of a Tymovirus, preferably that contained in the Turnip yellow mosaic virus genome (Matsuda and Dreher, 2004, *Virology,* 321, 36-46).

The sequence consisting, from the 5' end to the 3' end, of an upstream pseudoknot and of a tRNA-like structure is called a PKTLS sequence. The PKTLS sequence that can be aminoacylated by valine (PKTLS$^{val}$) of TYMV has been described by Matsuda and Dreher, 2004 (mentioned above).

According to another advantageous embodiment of the invention, said tRNA-like structure that can be aminoacylated by valine is combined, in the 3' position, with a ribozyme that is self-cleaving in cis in the 5' position (called cis-ribozyme). The autocatalytic cleavage of the cis-ribozyme makes it possible to free the 3' end (—CC or —CCA) of the tRNA-like structure that can be aminoacylated by valine.

The cis-ribozyme is particularly advantageous when the nuclear genome of a plant cell is transformed with a polydeoxyribonucleotide expressing, via an RNA polymerase II, a composite polyribonucleotide comprising a polyribonucleotide as defined above. Thus, in the transformed cells, the polyribonucleotide is expressed in the nucleus via the RNA polymerase II, generating a composite polyribonucleotide with a 5' cap and a 3' polyadenylation (polyA tail). The cis-ribozyme then self-cleaves and is eliminated with the polyA tail, freeing the 3' end (—CC or CCA) of the TLS$^{val}$ sequence. The resulting polyribonucleotide (comprising the trans-ribozyme and the TLS$^{val}$ sequence) is then exported from the nucleus to the cytosol, and then imported from the cytosol into the mitochondria by means of the TLS$^{val}$ sequence. Once in the mitochondria, the trans-ribozyme in turn exercises its function of cleavage of the target mitochondrial RNA.

Cis-ribozymes that can be used in the context of the present invention are known in themselves to those skilled in the art (for review, see Rossi, 2007, *Proc Natl Acad Sci*

USA, 104, 14881-14882). By way of nonlimiting examples, mention may be made of the cis-ribozymes derived from the genome of a virus, such as the Hepatitis Delta virus (HDV) (Perrotta and Been, 1991, *Nature,* 350, 434-436) or from a viroid (Daros et al., 2006, *EMBO Rep,* 7, 593-598).

Preferably, the cis-ribozyme is derived from the genome of a virus, and more preferably from a Hepatitis Delta virus.

By way of nonlimiting example of mitochondrial messenger RNA that can be targeted by a trans-ribozyme included in a composite RNA sequence in accordance with the invention, mention may be made of the mRNA of the plant atp9 gene. The cleavage of this mRNA has the effect of inducing, in a plant, cytoplasmic male sterility.

Thus, a particular example of a polyribonucleotide according to the present invention consisting of a trans-ribozyme directed against the mRNA of the mitochondrial atp9 gene, a linker sequence and the PKTLS sequence derived from the TYMV virus is represented in FIG. 1 and by the sequence SEQ ID No. 2.

By way of nonlimiting examples of noncoding mitochondrial RNAs which can be targeted by a trans-ribozyme included in a composite RNA sequence in accordance with the invention, mention will be made of the mnc1 RNA (SEQ ID No. 41) or the or78 RNA (SEQ ID No. 50).

Figure 11:
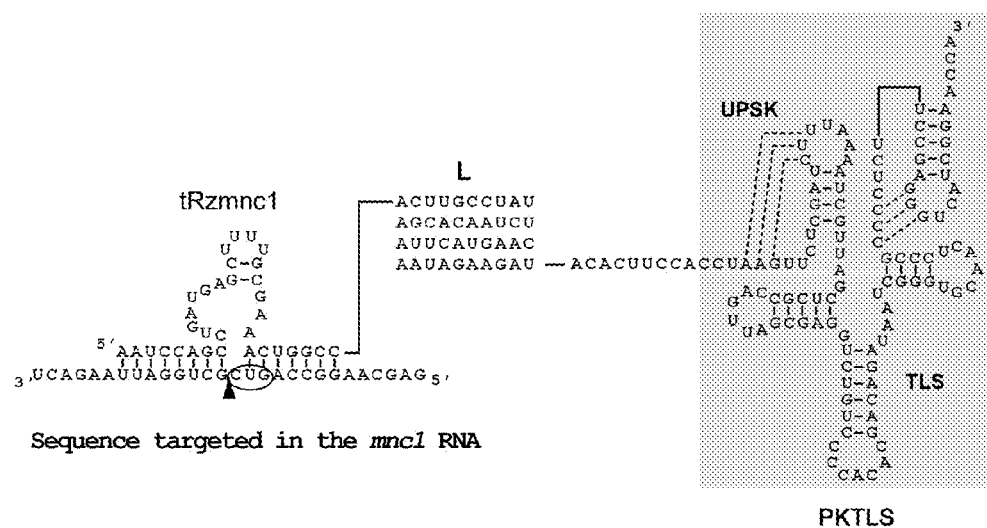

An example of a polyribonucleotide according to the present invention, consisting of a trans-ribozyme directed against the mnc1 mitochondrial RNA, a linker sequence and the PKTLS sequence derived from the TYMV virus, is represented in FIG. 11 and by the sequence SEQ ID No. 40.

Figure 15:
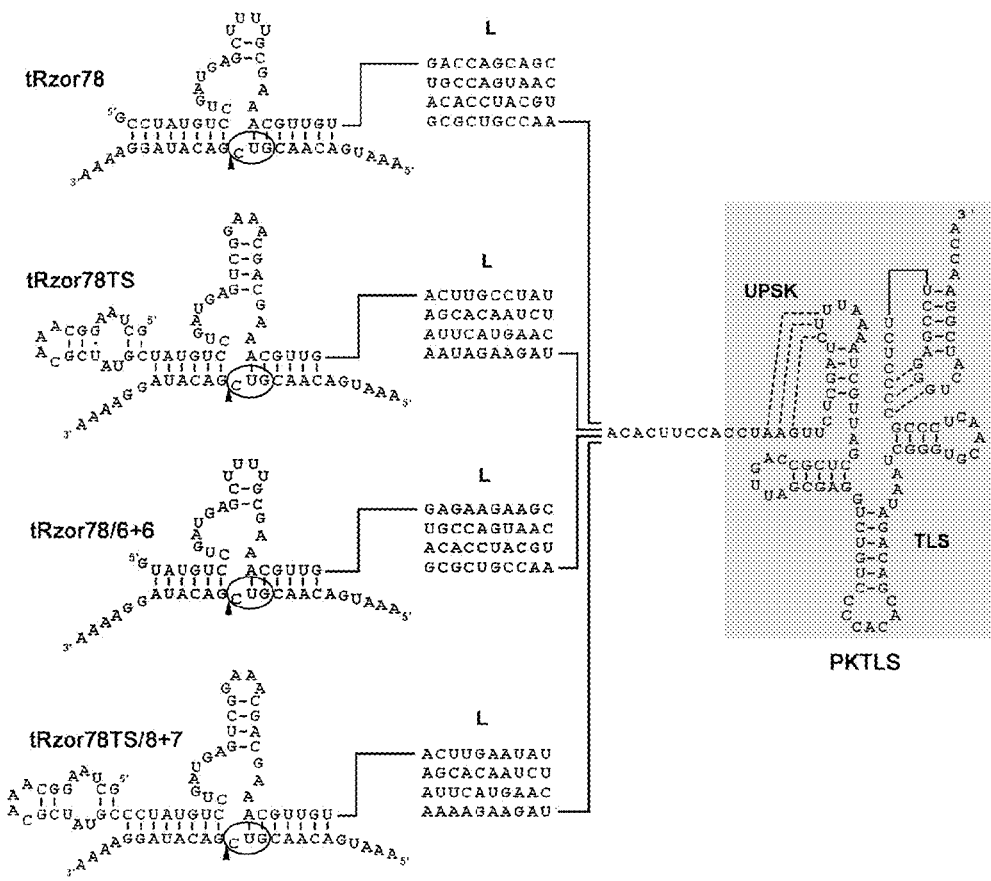

Examples of polyribonucleotides according to the present invention, consisting of a trans-ribozyme directed against the or78 mitochondrial RNA, a linker sequence and the PKTLS sequence derived from the TYMV virus, are represented in FIG. 15 and by the sequences SEQ ID Nos. 49, 58, 59 and 60.

A subject of the present invention is also the use of a tRNA-like structure that can be aminoacylated by valine ($TLS^{val}$), preferably combined with an upstream pseudoknot, as defined above, for importing a trans hammerhead ribozyme as defined above into the mitochondria of plant cells.

A subject of the present invention is also a polydeoxyribonucleotide (DNA) expressing a polyribonucleotide as defined above.

A particular example of a polydeoxyribonucleotide according to the present invention, expressing a trans-ribozyme directed against the mRNA of the mitochondrial atp9 gene, a linker sequence, the PKTLS sequence derived from the TYMV virus and the cis-ribozyme of the HDV virus, is represented by the sequence SEQ ID No. 1.

Another particular example of a polydeoxyribonucleotide according to the present invention, expressing a trans-ribozyme directed against the mnc1 mitochondrial RNA, a linker sequence, the PKTLS sequence derived from the TYMV virus and the cis-ribozyme of the HDV virus, is represented by the sequence SEQ ID No. 47.

Another particular example of a polydeoxyribonucleotide according to the present invention, expressing a trans-ribozyme directed against the or78 mitochondrial RNA, a linker sequence, the PKTLS sequence derived from the TYMV virus and the cis-ribozyme of the HDV virus, is represented by the sequence SEQ ID No. 56.

A subject of the present invention is also a recombinant expression cassette comprising a polydeoxyribonucleotide as defined above under the control of an appropriate transcription promoter.

Said transcription promoter may be any promoter that is functional in a cell, preferably a plant cell, i.e. capable of directing the transcription of a polydeoxy-ribonucleotide as defined above in a cell, preferably a plant cell (for review, see, for example, Yoshida and Shinmyo, 2000, *J Biosci Bioeng.,* 90, 353-362). The choice of the most appropriate promoter depends in particular on the organ(s) or on the tissue(s) targeted for the expression. The promoter may be a constitutive promoter (i.e. a promoter which is active in most tissues and cells and under most environmental conditions), a cell-type-specific promoter (i.e. a promoter which is active only or mainly in certain tissues or certain types of cells) or an inducible promoter (i.e. a promoter which is activated by physical processes or chemical stimuli). It is preferably a promoter for nuclear RNA polymerase II.

By way of nonlimiting examples of constitutive promoters which are commonly used in plant cells, mention may be made of the cauliflower mosaic virus (CaMV) 35S promoter, the NOS (nopaline synthase) promoter, the PG10-90 synthetic promoter (Ishige et al., 1999, *Plant J.,* 18, 443-448), preferably the 35S promoter.

By way of nonlimiting examples of organ-specific or tissue-specific promoters, mention may be made of promoters which are pollen- and/or anther-specific, such as the promoter of the corn Zmg13 gene (Guerrero et al., 1990, *Mol Gen Genet.,* 224, 161-168 and Hamilton et al., 1998, *Plant Mol Biol.,* 38, 663-669), the promoter of the cotton G9 gene (John and Petersen et al., 1994, *Plant Mol Biol.,* 26, 1989-1993), the soya Osg6B promoter (Tsuchiya et al., 1995, *Plant Cell Physiol.* 36, 487-494), the promoters of the rice OSIPA and OSIPK genes (Gupta et al., 2007, *Plant Cell Rep.,* 26, 1919-1931), the promoter of the turnip BcA9 gene (Lee et al., 2003, *Plant Cell Rep.,* 22, 268-273), the petunia chiA $P_{A2}$ and chiB $P_B$ promoters (Van Tunen et al., 1990, *Plant Cell,* 2, 393-401), the promoters of the tomato LAT52, LAT56 or LAT59 genes (Tovell et al., 1991, *Genes Dev.,* 5, 496-507 and Eyal et al., 1995, *Plant Cell.,* 7, 373-384), the promoter of the tobacco g10 gene (Rogers et al., 2001, *Plant Mol Biol.,* 45, 577-585), the promoter of the pea END1 gene (Gomez et al., 2004, *Planta,* 219, 967-981 and Roque et al., 2007, *Plant Cell Rep.* 26, 313-325), the promoter of the *Brassica* SLG gene (Thorsness et al., 1993, *Plant Cell.,* 5, 253-261) and the chimeric PSC promoter (Liu et al., 2008, *Plant Cell Rep.,* 27, 995-1004).

By way of nonlimiting examples of inducible promoters, mention may be made of the TetR (tetracycline-inducible), GVE/VGE (tebufenozide-inducible or methoxyfenozide-inducible), GVG, pOp/LhG4 and pOp6/LhGR (dexamethasone-inducible), XVE (estradiol-inducible) (Zuo et al., 2000, *Plant J.,* 24, 265-273), EcR (steroid-inducible) and AlcR (inducible in particular with ethanol) systems (for review, see Moore et al., 2006, *Plant J.,* 45, 651-683 and Padidam et al., 2003, *Curr. Opin. Plant Biol.,* 6, 169-177).

Said recombinant expression cassette also comprises a transcription terminator, such as, for example, the CaMV 35S terminator, the NOS terminator or the T9 terminator of the rbcS E9 gene (Zuo et al., 2000, mentioned above; Ishige et al., 1999, mentioned above).

A subject of the present invention is also a recombinant vector comprising a polydeoxyribonucleotide or an expression cassette as defined above.

The expression cassettes and the expression vectors in accordance with the invention can, of course, also comprise other sequences, usually employed in constructs of this type, such as translation leader (TL) sequences, polyadenylation sites, and also, where appropriate, amplifying sequences (transcription enhancer sequences). They can also comprise sequences which make it possible to monitor the transformation, and also to identify and/or to select the cells or organisms transformed. These are, in particular, reporter genes (for example the beta-glucuronidase (GUS) gene, the luciferase gene or the green fluorescent protein (GFP) gene), conferring an easily recognizable phenotype on these cells or organisms, or else selection marker genes (for example, genes for resistance to an antibiotic, such as kanamycin or hygromycin, or to a herbicide).

The choice of the promoter and of the additional sequences that can be inserted into the expression cassettes and vectors in accordance with the invention, and also that of the host vector, can be made, conventionally, by those skilled in the art according in particular to criteria such as the host cells and organisms chosen, the desired expression profile in the host cell or organism, the genetic transformation protocols envisioned, etc.

The present invention also encompasses a host cell comprising an expression cassette or a recombinant vector as defined above.

The host cells can be prokaryotic or eukaryotic cells. In the case of prokaryotic cells, they may in particular be agrobacteria such as *Agrobacterium tumefaciens* or *Agrobacterium rhizobium*. In the case of eukaryotic cells, they may in particular be plant cells stemming from dicotyledonous or monocotyledonous plants, for instance tobacco cells.

A subject of the present invention is also plants genetically transformed with at least one polydeoxy-ribonucleotide or one expression cassette in accordance with the invention, and in particular transgenic plants comprising, in their nuclear genome, at least one copy of a transgene containing a polydeoxyribonucleotide in accordance with the invention.

A transgenic plant is herein defined as a transformed plant in which the exogenous genetic information provided by the transforming polydeoxyribonucleotide is stably integrated into the chromosomal DNA, in the form of a transgene, and can thus be transmitted to the progeny of said plant. This definition therefore also encompasses the progeny of the plants resulting from the initial transgenesis, as long as they contain a copy of the transgene in their genome.

Various methods for obtaining transgenic plants are well known in themselves to those skilled in the art. Generally, these methods involve transforming plant cells, regenerating plants from the transformed cells, and selecting the plants which have integrated the transgene.

A very large number of techniques for transforming plant germinal or somatic cells (isolated, in the form of tissue or organ cultures, or on the whole plant), and regenerating the plants are available. The choice of the most suitable method generally depends on the plant concerned.

The plant material (protoplasts, cells, calluses, leaves, cuttings, seeds, etc.) obtained from the transformed cells or from the transgenic plants in accordance with the invention is also a part of the subject of the present invention. The invention also encompasses the products obtained from the transgenic plants in accordance with the invention, in particular fodder, wood, leaves, stems, roots, flowers and fruits.

A subject of the present invention is also a method for obtaining a transgenic plant having cytoplasmic male sterility, comprising the following steps:
a) obtaining a plant cell comprising an expression cassette comprising a sequence expressing a hammerhead ribozyme directed against the atp9 mRNA, the mnc1 RNA or the or78 RNA, as defined above, preferably directed against the atp9 mRNA, and b) regenerating, from the plant cell obtained in step a), a transgenic plant expressing said hammerhead ribozyme directed against the atp9 mRNA, the mnc1 RNA or the or78 RNA.

The present invention also encompasses a transgenic plant that can be obtained by means of the method described above.

The present invention applies to dicotyledonous or monocotyledonous plants. By way of nonlimiting examples, it can apply to plants of the family Poaceae, Papillonaceae, Cruciferae, Umbelliferae, Solanaceae, Leguminosae, Labiatae or Asteraceae, and more particularly to corn, wheat, barley, rye, triticale, oats, rapeseed, cabbage, tobacco, pea, tomato, alfalfa, beetroot, sunflower, soya and rice.

The present invention will be understood more clearly by means of the additional description which follows, which refers to nonlimiting examples illustrating the use of a PKTLS sequence for importing a trans-ribozyme into plant cell mitochondria, and also the attached figures:

FIG. 1: Recombinant RNA (SEQ ID No. 2) constructed for the strategy for cleaving the atp9 mRNA in mitochondria. The trans-ribozyme (tRzatp9) is represented interacting with its target sequence. It is combined with the PKTLS sequence of TYMV (the $TLS^{val}$ sequence corresponding to the last 82 nucleotides in the 3' position) by a linker sequence (L). The sequence recognized by the ribozyme is an AUC triplet (circled) and the cleavage takes place after the cytosine (C) (arrow).

Figure 2:
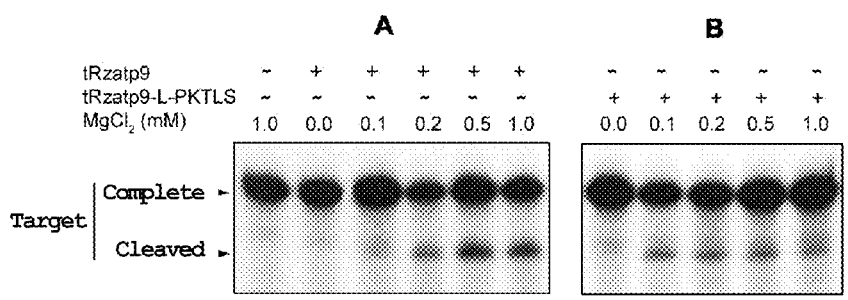

FIG. 2: Cleavage activity of the tRzatp9 trans-ribozyme alone (A) or combined with the PKTLS of TYMV in the RNA tRzatp9-L-PKTLS (B). The activity was determined according to the $MgCl_2$ concentration. The reactions were carried out for 1 hour under standard conditions in the presence of increasing concentrations of $MgCl_2$ and with a ribozyme/target molar ratio of 10/1. The cleavage products were analyzed by polyacrylamide gel electrophoresis.

Figure 3:
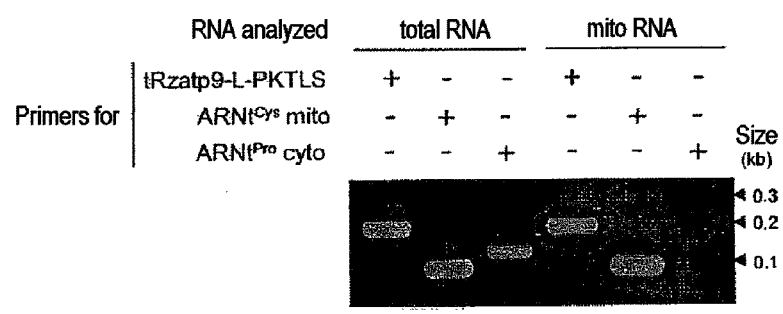

FIG. 3: Analysis by agarose gel electrophoresis of the RT-PCR products obtained from total or mitochondrial RNA of tobacco cells transformed with the plasmid pER8-tRzatp9LPKTLScHDV and induced with estradiol.

Figure 4:
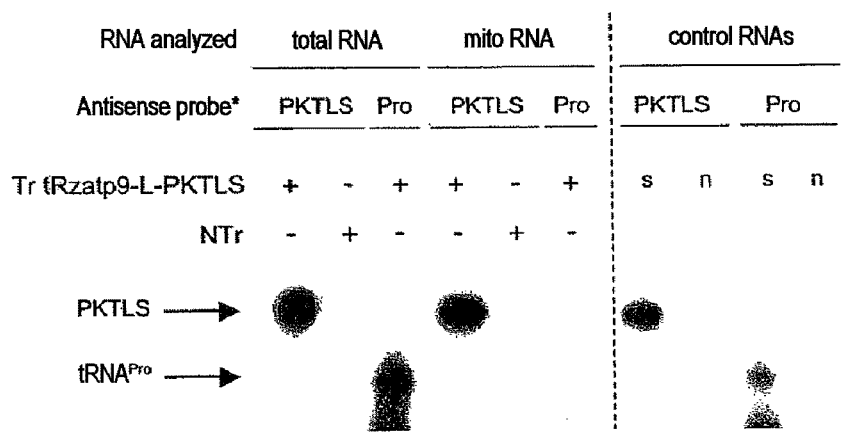

FIG. 4: Analysis by polyacrylamide gel electrophoresis of radioactive antisense RNAs (*) protected against ribonucleases in the presence of total or mitochondrial RNA of tobacco cells transformed with the plasmid pER8-tRzatp9LPKTLScHDV and induced with estradiol. Tr tRzatp9-L-PKTLS=RNA of transformed tobacco cells; NTr=RNA of nontransformed tobacco cells. The arrow indicates the expected protection product; Pro=cytosolic $tRNA^{Pro}$ probe; s=positive control for size resulting from the reaction for ribonuclease protection by a sense in vitro transcript; n=negative control resulting from a ribonuclease protection reaction carried out with the antisense probe alone.

Figure 5:
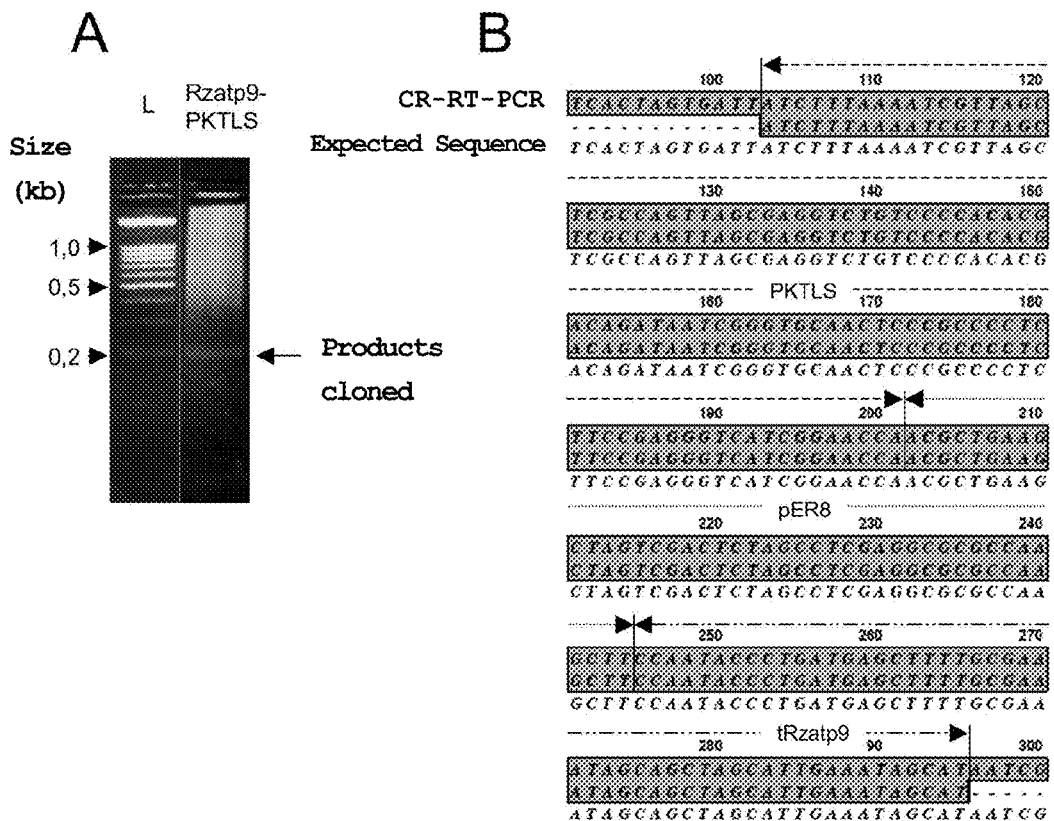

FIG. 5: Analysis of the products of the CR-RT-PCR carried out after circularization of RNA from tobacco cells transformed with the plasmid pER8-tRzatp9LPKTLScHDV and induced with estradiol. (A) agarose gel electrophoresis; the lane marked L corresponds to the size marker. Only the final nested 5 PCR is represented. (B) alignment of the sequence of the cloned CR-RT-PCR products (SEQ ID No. 67) and of the sequence expected from the construct (SEQ ID No. 68); key overlapping sequence (SEQ ID. No. 69). PKTLS: 5' part of the PKTLS sequence of TYMV; pER8: pER8 vector region transcribed with the construct; tRzatp9: part of the 10 trans-ribozyme.

Figure 6:
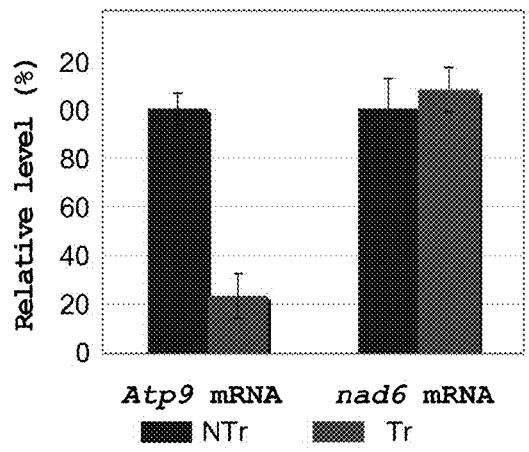

FIG. 6: Analysis by qRT-PCR of the level of the atp9 mRNA and the nad6 mRNA (subunit 6 of respiratory chain complex I, NAD(P)H dehydrogenase) in the RNAs extracted from nontransformed tobacco cells (NTr) or tobacco cells transformed with the plasmid pER8-tRzatp9LPKTLScHDV (Tr), both types of cells being induced with estradiol. The results are made uniform relative to the actin mRNA and to the rpl2 mitochondrial ribosomal protein mRNA.

Figure 7:
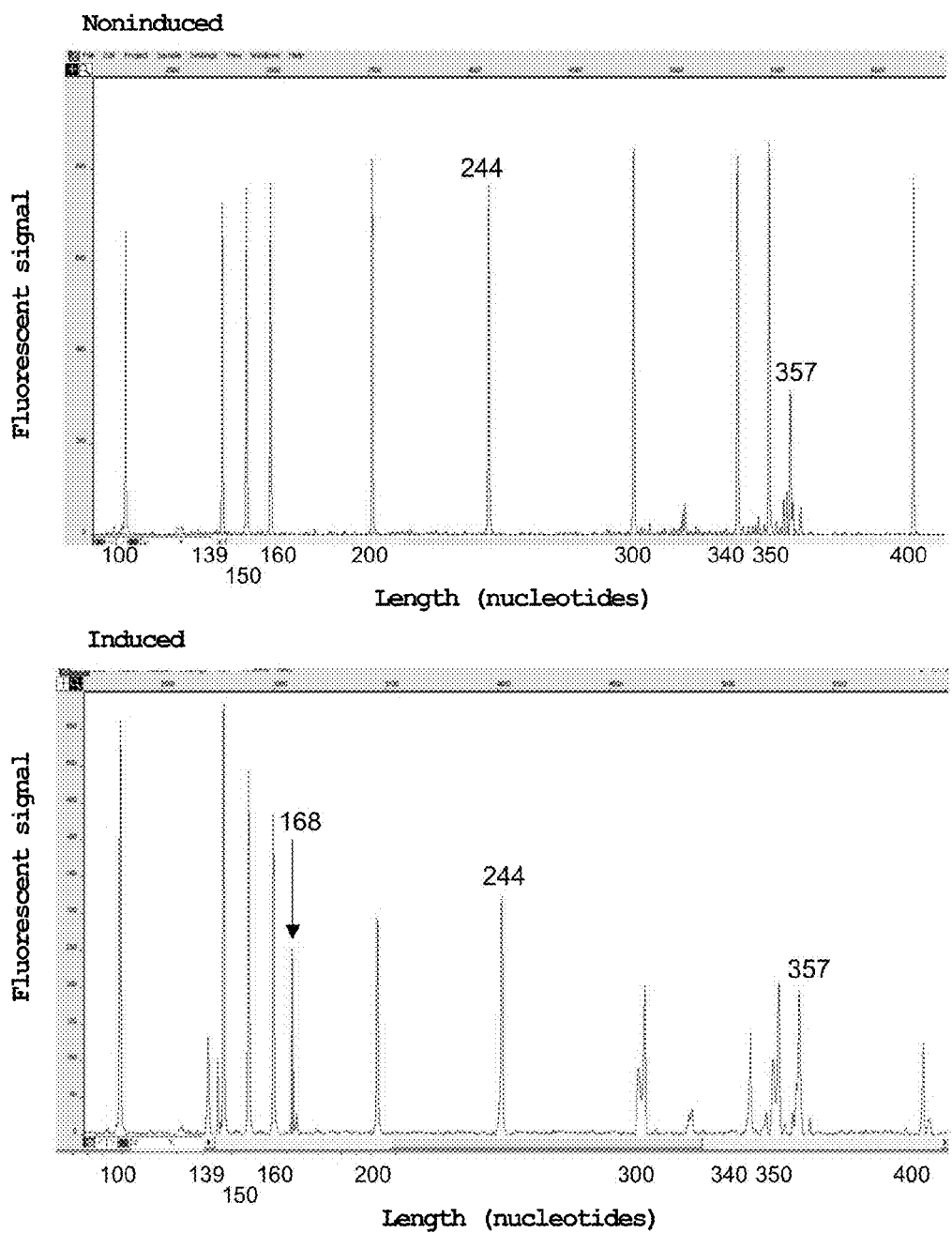

FIG. 7: Analysis by fluorescently labeled primer extension of the atp9 transcripts in the RNAs extracted from tobacco cells transformed with the plasmid pER8-tRzatp9LPKTLScHDV and induced or not induced with estradiol. The product of specific cleavage by the tRzatp9 ribozyme (168 nucleotides) is indicated with an arrow. The values along the x-axis correspond to size markers.

Figure 8:
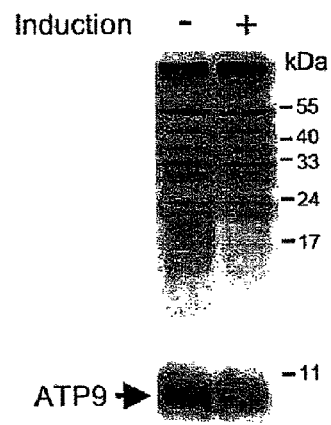

FIG. 8: Polyacrylamide gel analysis of the products of in organello translation in the presence of [$^{35}$S]methionine in mitochondria isolated from tobacco cells transformed with the plasmid pER8-tRzatp9LPKTLScHDV and induced or not induced with estradiol. The migration of the ATP9 protein is indicated.

Figure 9:
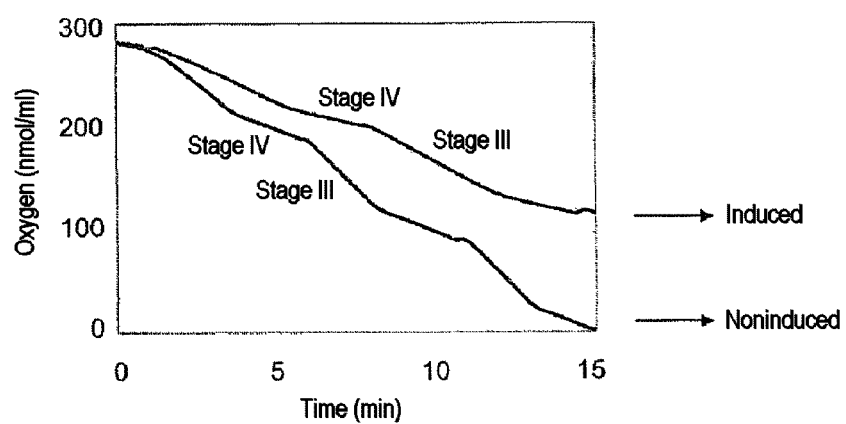

FIG. 9: Measurement, in an oximeter, of the respiratory activity of the mitochondria isolated from tobacco cells transformed with the plasmid pER8-tRzatp9LPKTLScHDV and induced or not induced with estradiol. Stage IV, respiration in the absence of ADP; stage III, respiration after the addition of ADP at a final concentration of 200 μm.

Figure 10:
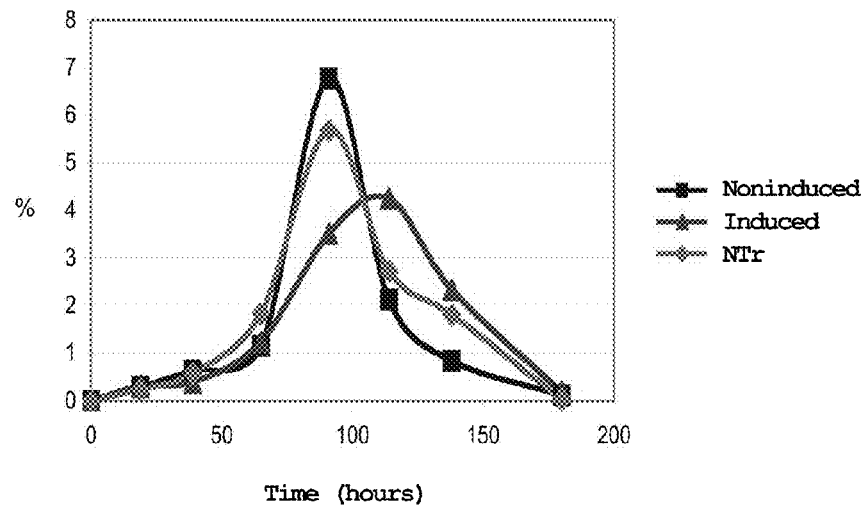

FIG. 10: Growth rate of tobacco cells transformed with the plasmid pER8-tRzatp9LPKTLScHDV and induced or not induced with estradiol. NTr=nontransformed cells.

FIG. 11: Recombinant RNA (SEQ ID No. 40) constructed for the strategy of cleavage of mnc1 RNA in plant cell mitochondria. The trans-ribozyme (tRzmnc1) is presented interacting with its target sequence. It is combined with the PKTLS sequence of TYMV by means of a linker sequence (L). The sequence recognized by the ribozyme is a GUC triplet (circled) and the cleavage takes place after the cytosine (C) (arrow).

Figure 12:
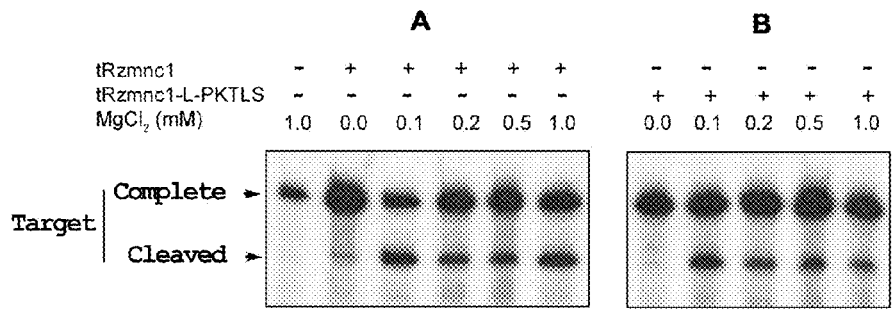

FIG. 12: Cleavage activity of the tRzmnc1 trans-ribozyme alone (A) or combined with the PKTLS of TYMV in the RNA tRzmnc1-L-PKTLS (B). The activity was determined according to the concentration of MgCl$_2$. The reactions were carried out for 1 hour under standard conditions in the presence of increasing concentrations of MgCl$_2$ and with a ribozyme/target molar ratio of 10/1. The cleavage products were analyzed by polyacrylamide gel electrophoresis.

Figure 13:
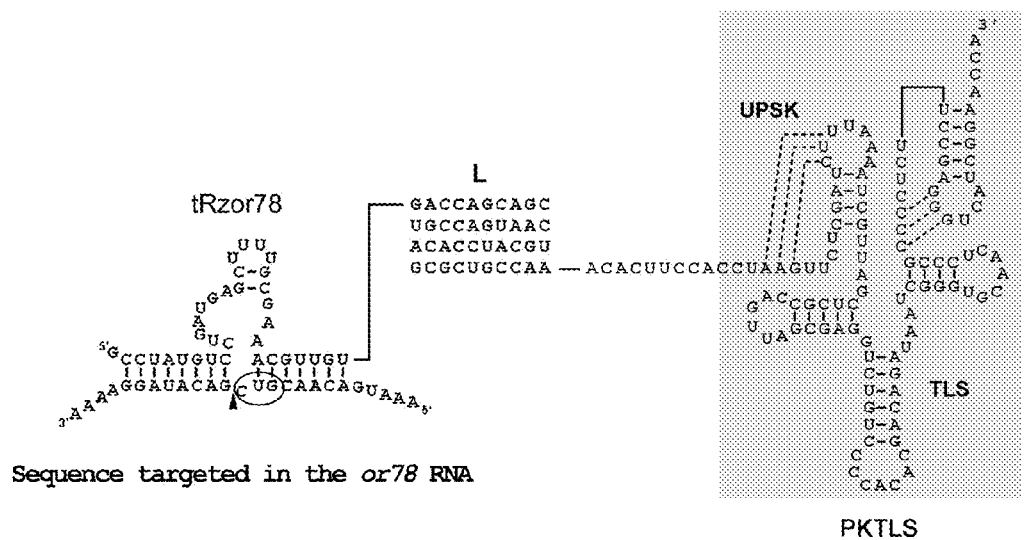

FIG. 13: Recombinant RNA (SEQ ID No. 49) constructed for the strategy of cleavage of or78 RNA in plant cell mitochondria. The trans-ribozyme (tRzor78) is presented interacting with its target sequence. It is combined with the PKTLS sequence of TYMV by means of a linker sequence (L). The sequence recognized by the ribozyme is a GUC triplet (circled) and the cleavage takes place after the cytosine (C) (arrow).

Figure 14:
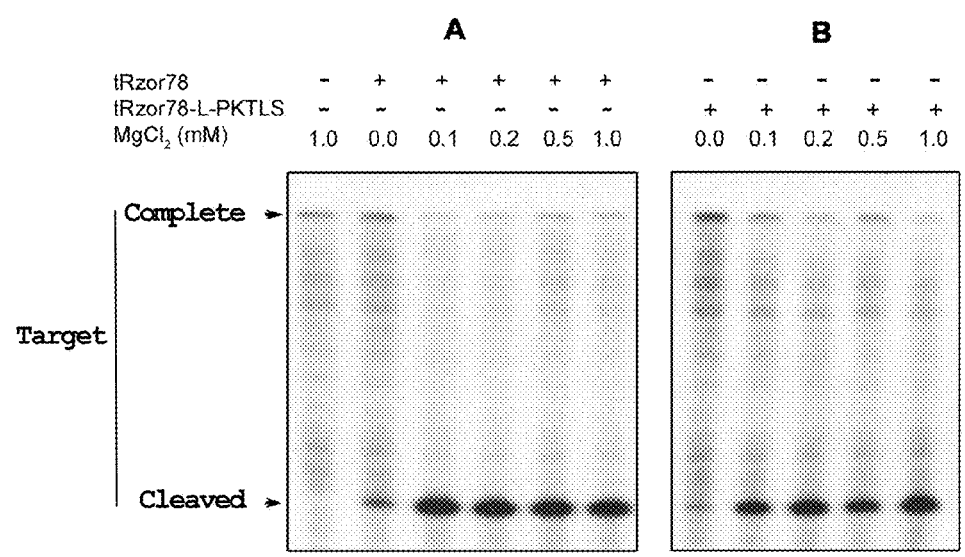

FIG. 14: Cleavage activity of the tRzor78 trans-ribozyme alone (A) or combined with the PKTLS sequence of TYMV in the RNA tRzor78-L-PKTLS (B). The activity was determined according to the concentration of MgCl$_2$. The reactions were carried out for 1 hour under standard conditions in the presence of increasing concentrations of MgCl$_2$ and with a ribozyme/target molar ratio of 10/1. The cleavage products were analyzed by polyacrylamide gel electrophoresis.

FIG. 15: Recombinant RNAs (SEQ ID Nos. 49, 58, 59 and 60) constructed for the cleavage of or78 RNA (SEQ ID No. 50) in plant cell mitochrondria. The trans-ribozymes (tRzor78, tRzor78TS, tRzor78/6+6 and tRzor78TS/8+7) are represented interacting with their target sequence. They are combined with the PKTLS sequence of TYMV by means of a linker sequence (L). The sequence recognized by the ribozyme is a GUC triplet (circled) and the cleavage takes place after the cytosine (C) (arrow).

Figure 16:
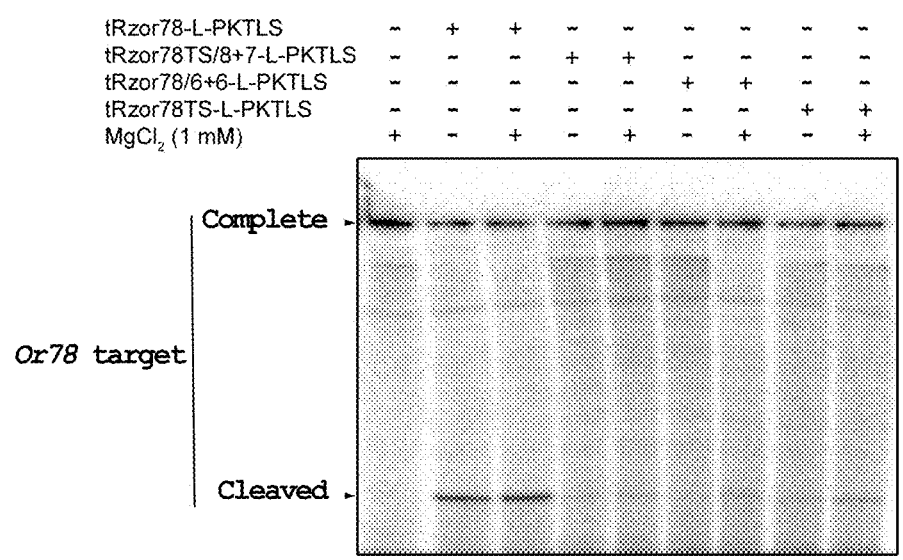

FIG. 16: Cleavage activity of the recombinant RNAs tRzor78-L-PKTLS (SEQ ID No. 49), tRzor78TS/8+7-L-PKTLS (SEQ ID No. 60), tRzor78/6+6-L-PKTLS (SEQ ID No. 59) and tRzor78TS-L-PKTLS (SEQ ID No. 58). The reactions were carried out for 1 hour under standard conditions, optionally in the presence of 1 mM of MgCl$_2$, and with a ribozyme/target RNA molar ratio of 10/1. The cleavage products were analyzed by polyacrylamide gel electrophoresis.

EXAMPLE I

Use of the PKTLS Sequence of TYMV for Importing into Plant Cell Mitochondria A Trans Hammerhead Ribozyme Directed Against the atp9 mRNA An antisense strategy in plant cell mitochondria, based on a trans hammerhead ribozyme, was developed. Trans hammerhead ribozymes carry their own RNA cleavage activity and do not require other factors. The major mitochondrial mRNA atp9 encoding subunit 9 of ATP synthase was chosen as target to be cleaved in the organelles. Its sequence is highly conserved from one plant species to the other. FIG. 1 shows the elements of the recombinant RNA constructed for this strategy. The trans-ribozyme directed against the atp9 mRNA (tRzatp9) is combined with the PKTLS sequence of TYMV by means of a linker sequence (L) which has a low structuring potential, intended to avoid interactions between the various elements of the genetic construct.

I. Materials & Methods

Linker RNA Sequence (L):

The L sequence was developed by bioinformatics. A random sequence of 40 nucleotides was first defined by computer and then specifically refined according to each passenger sequence using the MFOLD secondary structure prediction software (Mathews et al., 1999, *J Mol Biol.*, 288, 911-940).

Obtaining the Plasmid pCK-SPTYPKTLScHDV:

The cHDV sequence was first amplified from a preexisting recombinant plasmid pSA1 (Perrotta et al., 1991, *Nature*, 350, 434-436) using the direct primer 5'-CATCGGAACCA-GGGTCGGCATGGCA-3' (SEQ ID No. 3), straddling the sequences to be fused, and the reverse primer 5'-GGTC TCTAGACTCCCTTAGCCAT-3' (SEQ ID No. 4) carrying an XbaI site (underlined). The product of the first PCR reaction was used as a "megaprimer" at the same time as the direct primer 5'-GAC<u>GGATCC</u>CCCGCATCGACCTG-3' (SEQ ID No. 5) carrying a BamHI site (underlined) so as to obtain the whole of the construct, taking as template the preexisting plasmid pTYMC carrying the genomic sequence of TYMV (Weiland and Dreher, 1989, *Nucleic Acids Res.*, 17, 4675-4687). The fragment obtained was subsequently introduced into the plasmid pCK-GFPS65C between the BamHI and XbaI sites located 3' of the GFP gene, producing the plasmid pCK-GFPS65C-SPTYPKTLScHDV. The plasmid pCK-GFPS65C results from the insertion of the GFPS65C (green fluorescent protein) gene (Heim et al., 1995, *Nature* 373, 663-664) into the expression plasmid pRTL2 (Carrington et al., 1991, *Plant Cell*, 3, 953-962). It possesses the strong double 35S promoter of the cauliflower mosaic virus (CaMV) coupled to a translation leader sequence TL of the tobacco etch virus (TEV). Located downstream of the gene encoding GFP is the CaMV 35S terminator.

The plasmid pCK-GFPS65C-SPTYPKTLScHDV was digested with the XhoI and BamHI restriction enzymes, which made it possible to eliminate the TL sequence and the GFP gene. The sticky ends were filled in using the *Escherichia coli* DNA polymerase I Klenow fragment, in order to obtain blunt ends. The plasmid was subsequently recircularized, generating the plasmid pCK-SPTYPKTLScHDV, the sequences meaning that an XhoI restriction site was conserved.

In vitro DNA Transcription:

The RiboMAX™ kit (Promega) is used for the in vitro DNA transcription reactions. All the constructs are placed under the control of the T7 phage RNA polymerase promoter. The transcription is carried out for 2 hours at 37° C. in a reaction volume of 20 µl which comprises: 2 µg of linearized DNA (resulting from PCR or from plasmid DNA), 4 µl of 5× T7 transcription buffer, 6 µL of rNTPs (each at 25 mM) and 2 µL of the T7 mix solution containing the polymerase. For the radioactive transcriptions, only the amount of rNTPs varies. Two microliters of rNTPs (ATP, GTP and CTP at 2.5 mM and UTP at 250 µM) and also 40 µCi of [$\alpha^{32}$P]UTP are introduced into the reaction.

In both cases, after synthesis, 3 units of RNase-free DNase are added and the volume is made up to 50 µL. Incubation at 37° C. for 15 min is necessary in order to digest the DNA. In order to remove the nucleotides not incorporated during the in vitro transcription and the DNA degradation products, the reaction medium is subsequently deposited on a 1 mL Sephadex G-50 column dried beforehand by centrifugation at 200×g for 2 min. Elution is carried out by further centrifugation under the same conditions.

In vitro Cleavage Tests:

The cleavage reactions were carried out under the following conditions: 15 nM of nonradioactive target RNA and 50 fmol (30 000 cpm) of radioactive target RNA labeled with [$^{32}$P] were incubated at 25° C. for 1-5 hours in a 50 mM Tris-HCl buffer at pH 7.5 in the presence of 150 nM of tRzatp9 trans-ribozyme alone or of tRzatp9-L-PKTLS RNA. Before the cleavage reaction, the target RNA and the catalytic RNA were denatured for 2 min at 75° C. and then left to cool slowly to 25° C. in a heating block (1° C./min). Various concentrations of $MgCl_2$ were subsequently added for the cleavage reaction (final reaction medium 10 µL). The cleavage products were separated by electrophoresis on an 8% or 10% (w/v) polyacrylamide gel in the presence of 8 M urea in a 90 mM Tris-borate buffer containing 2 mM of EDTA (1×TBE). The gels were dried and subjected to autoradiography.

Plant Cell Transformation:

*Agrobacterium tumefaciens* bacteria (strain LBA4404) carrying the construct of interest in the plasmid pER8 (Zuo et al., 2000, Plant J., 24, 265-273) are cultured in an LB medium supplemented with $MgSO_4$ (2 mM), sucrose (5 g/L) and rifampicin (25 µg/mL) or spectinomycin (100 µg/mL) for 2 days at 28° C. with shaking. The BY-2 (Bright Yellow 2; Nagata et al., 1992, Int Rev Cyt., 132, 1-30) tobacco (*Nicotiana tabacum*) cell suspensions are cultured at 25° C. in the dark. The day before they are cocultured with the tobacco cells, the bacteria are subcultured in the same fresh medium. On the day of the coculture, the bacteria are taken up in 1.5 mL of LB medium. Four milliliters of a 3-day culture of BY-2 tobacco cells are placed in a Petri dish and 100 µL of bacteria are added. In order to promote transformation of the plant cells with *A. tumefaciens*, acetosyringone is added at a concentration of 200 µM. The coculture is subsequently maintained at 27° C. with shaking and in the dark for 3 days.

Transformant Selection:

In order to eliminate the bacteria present as much as possible, the BY-2 cells are washed several times successively with culture medium. Two milliliters of cell suspension are subsequently plated out on dishes containing culture medium with 0.8% (w/v) agar and hygromycin (20 µg/mL) for selection of the tobacco transformants, and carbenicillin at 500 µg/mL for elimination of the residual agrobacteria. The first resistant calluses appear 2 to 3 weeks after transformation. They are maintained on hygromycin medium at 25° C. in the dark and subcultured on a fresh medium once a month. Cultures in liquid suspension maintaining the selection pressure with hygromycin are developed from these calluses for the analyses, in particular for the preparation of isolated mitochondria.

Extraction of Total RNA:

A two-milliliter sample of BY-2 tobacco cell culture is taken. After centrifugation for 5 min at 14 000×g, the cells are resuspended in 1 mL of TriReagent® (Molecular Research Centre, Inc.) and left at ambient temperature for 5 min. After the addition of 200 µL of chloroform, the samples are vigorously agitated for 15 sec and then left at ambient temperature for 15 min. Centrifugation for 15 min at 12 000×g makes it possible to separate the aqueous phase from the phenolic phase. The aqueous phase contains the RNAs and little DNA. The RNAs are precipitated by adding 500 µL of isopropanol and sedimented by centrifugation for 8 min at 12 000×g. The pellet is washed with 1 mL of 75% ethanol and recovered by centrifugation at 7500×g for 5 min. After drying, the RNAs are redissolved in water.

Preparation of Tobacco Cell Mitochondria:

The cell cultures are filtered using a water-vacuum pump. Ten grams of cells are gently taken up, using a mortar, in 50 mL of enzymatic solution (1 mg/mL pectolyase Y23, 10 mg/mL cellulase Onozuka RS, 0.45M mannitol, 3.6 mM MES-KOH pH 5.5) without rupturing the cells, and placed in a Petri dish. The digestion is carried out for 2 hours at 30° C., in the dark with agitation (70 revolutions per min). The protoplasts are subsequently sedimented by centrifugation for 5 min at 800×g and washed with 50 mL of protoplast buffer (0.3M sucrose, 10 mM potassium phosphate pH 7.5, 1 mM EDTA, 0.1% w/v BSA, 5 mM glycine). This washing step is repeated a second time.

Once washed, the protoplasts are taken up in 40 mL of grinding buffer (0.3 M sucrose, 30 mM sodium diphosphate, 2 mM EDTA, 0.3% w/v BSA, 0.8% w/v PVP 25 000, pH adjusted to 7.5 with concentrated HCl before adding: 0.05% w/v cysteine, 5 mM glycine, 2 mM β-mercaptoethanol). The protoplasts are broken by filtration through a nylon cloth (30 µM mesh opening) under pressure, using a cut syringe. The cell debris is sedimented by centrifugation for 15 min at 2000×g. The mitochondria contained in the supernatant are sedimented by further centrifugation for 15 min at 11 000×g. The mitochondrial pellet is taken up 500 µL of washing buffer (0.3M sucrose, 10 mM potassium phosphate pH 7.5, 1 mM EDTA, 0.1% w/v BSA, 5 mM glycine). The mitochondria are subsequently deposited on a discontinuous Percoll gradient (Sigma) of 13.5%, 21% and 45% v/v in 2×PB buffer (100 mM Tris-HCl pH 7.5, 0.5M sucrose, 6 mM EDTA). This gradient is prepared in 2.2 mL tubes containing 500 µL of 13.5% and 45% Percoll separated by 600 µL of 21% Percoll. 150 microliters of mitochondria taken up in washing buffer are deposited on the gradient. After centrifugation for 20 min at 14 000×g, the mitochondria located in the 21%-Percoll phase are removed and diluted 10 times in washing buffer containing no BSA, and then centrifuged for 10 min at 12 000×g in order to remove the Percoll. This step is followed by another washing/centrifugation step in the same washing buffer without BSA. The amount of mitochondria is evaluated by measuring the amount of proteins using the Bradford method (Bradford, 1976, *Anal Biochem.*, 72, 248-254). The mitochondria can subsequently be used directly in order to carry out respiration tests or for in organello protein synthesis tests.

If the mitochondria must be used to extract the RNAs, they are then treated with RNase in order to limit the possible cytosolic RNA contaminations. In this case, the crude mitochondrial pellet after centrifugation for 15 min at 11 000×g is taken up in 500 µL of washing buffer containing a solution of RNases (100 µg/mL of RNase A and 750 U/mL of RNase T1) and gently agitated for 20 min at 25° C. The RNase-treated mitochondria are then deposited on a discontinuous gradient of Percoll of 13.5%, 21% and 45% v/v in 2×PB buffer as described above. Successive washes are then carried out with a BSA-free washing buffer containing EDTA and EGTA at 5 mM, in order to inhibit the RNases still present. The RNA can be directly extracted from the final mitochondrial pellet.

Mitochondrial RNA Extraction:

200 µL of extraction solution (10 mM Tris-HCl pH 7.5, 10 mM $MgCl_2$, 1% w/v SDS) are added to one to five milligrams of mitochondria. The whole mixture is agitated vigorously for 2 min, and then centrifuged for 10 min at 10 000×g. The supernatant is extracted with phenol and then the nucleic acids are precipitated with ethanol. Successive DNase treatments then make it possible to eliminate the DNA.

RT-PCR Protocol:

The enzyme used to carry out the reverse transcription reaction is SuperScript™ III (Invitrogen). The protocol used is the one recommended by the manufacturer. Firstly, 300 ng to 5 µg of total or mitochondrial RNA are added to 2 pmol of the primer specific for the RNA being investigated or to 250 ng of a mixture of hexamers (in the case of quantitative RT-PCRs). One microliter of dNTPs (each 10 mM) is added and the volume is then made up to 13 µL. The mixture is incubated for 5 min at 65° C. and then immediately put on ice for at least 1 min. Four microliters of reaction buffer (250 mM Tris-HCl pH 8.3, 375 mM KCl, 15 mM $MgCl_2$) are then added as are 1 µL of 0.1M DTT, 40 units of RNase inhibitor (RNase out, Invitrogen) and 200 units of SuperScript™ III enzyme (200 U/µL in 20 mM Tris-HCl pH 7.5, 100 mM NaCl, 0.1 mM EDTA, 1 mM DTT, 0.01% v/v Nonidet P-40, 50% w/v glycerol). The samples are then placed at 25° C. for 5 min and then at 55° C. for one hour. In order to inactivate the reaction, an incubation at 70° C. for 15 min is carried out. The samples are directly used for the PCR reaction.

Ribonuclease Protection Assays:

The ribonuclease protection protocol is derived from the method described by Goodall et al., 1990 (*Methods Enzymol.*, 181, 148-161). A radioactive antisense RNA probe is synthesized by in vitro transcription. After ethanolic precipitation, the probe is redissolved in hybridization buffer (80% v/v formamide, 40 mM PIPES pH 6.7, 400 mM NaCl, 1 mM EDTA) and its radioactivity is counted. Eight hundred nanograms of total or mitochondrial RNA are precipitated and redissolved in 10 µL of hybridization buffer. The equivalent of 20 000 cpm of antisense probe is then added thereto and the volume is made up to 20 µL. Denaturation for 10 min at 95° C. is necessary before hybridization at 55° C. overnight. The antisense probe then hybridizes to the target RNA.

The following day, 200 µL of RNase solution (10 mM Tris-HCl pH 7.5, 5 mM EDTA, 100 mM LiCl, 200 mM NaCl, 100 µg/mL RNase A, 750 U/mL RNase T1) are added and the samples are incubated for 30 min at 30° C. in order to eliminate the nonhybridized RNAs and the unprotected ends of the radioactive antisense probe. Then, in order to eliminate the RNases A and T1, 6 µL of 10% w/v SDS and 6 µL of proteinase K (10 mg/mL) are added. After incubation for 15 min at 37° C., the samples are extracted with a phenol/chloroform (1/1) mixture, precipitated with ethanol, and then resuspended in loading buffer and separated on a denaturing 8% w/v polyacrylamide gel. The gel is subsequently dried and then visualized by autoradiography.

Protocol for RT-PCR on Circularized RNA (CR-RT-PCR):

A first reaction aims to eliminate the cap potentially present at the 5' end of the RNAs to be analyzed. This reaction is carried out using Tobacco Acid Pyrophosphatase (TAP) (Epicentre Biotechnologies). The RNAs are incubated for 30 min at 37° C. in a 50 mM sodium acetate buffer (pH 6.0) containing 0.1% v/v beta-mercaptoethanol, 1 mM EDTA and 0.01% v/v Triton X-100, in the presence of one unit of enzyme per nanomole of RNA, and of 2 mM ATP. The RNAs are then extracted with phenol and precipitated with ethanol before being circularized using T4 RNA ligase (Fermentas). Ten micrograms are incubated for 3 hours at 37° C. in the presence of 100 units of enzyme and 3.4 µM ATP in ligation buffer (50 mM HEPES-NaOH pH 8.0, 10 mM $MgCl_2$, 10 mM DTT). A reverse transcription reaction is then carried out in order to synthesize the cDNA corresponding to the ligation between the 5' and 3' ends of the RNA analyzed. An initial PCR reaction and then a nested PCR reaction are carried out in order to amplify this sequence and then to clone it into the vector pGEM®-TEasy (Promega). The amplicon is then sequenced.

qRT-PCR Protocol:

The primers are designed using the PrimerExpress software (Applied Biosystems). Their effectiveness is verified by means of the LinRegPCR software (bioinfo@amc.uva.nl) (Ramakers et al., 2003, *Neurosci Lett.*, 339, 62-66). All the analyses are carried out using the iQ5 software (Biorad). The PCR reactions are carried out in a reaction medium of 20 µL, composed of 10 µL of SybrGreen kit (MasterMix Plus, Eurogentec), 0.6 µM of direct and reverse primers and 1 µL of RT reaction (carried out with a mixture of hexamers). The volume is made up with water.

The program used is the following:
One cycle: –95° C., 30 sec
One cycle: –50° C., 2 min
 –95° C., 10 min
Forty cycles: –95° C., 1 min
 –60° C., 1 min
One cycle: –95° C., 1 min
 –55° C., 1 min
Eighty cycles: – from 55° C. to 94.5° C.; in increments of 0.5° C. every 10 sec.

The geNorm software (Vandesompele et al., 2002, *Genome Biol.*, 3, Research0034) made it possible to define the actin and rpl2 mitochondrial ribosomal protein genes as being the most stable. These genes were therefore used as references in the experiments.

Fluorescently Labeled Primer Extension Protocol (Fluorescently Labeled Oligonucleotide Extension, FLOE):

Five micrograms of mitochondrial RNA are used in a reverse transcription reaction using 5 nM of a probe which has been 5'-labeled with the ROX fluorescent molecule and which is complementary to the 3' coding end of the atp9 gene. The reaction is carried out in 30 µL. A second reaction is carried out by addition of dNTPs (1.5 mM), 40 U of RNase out (Invitrogen), 25 U of Superscript III enzyme (Invitrogen) and 1× buffer. The volume is made up to 40 µL. Ten microliters are then precipitated with ethanol and resuspended in 2 µl of water, to which 8 µL of GeneScan 500 ROX fluorescent size marker (Applied Biosystems), diluted to 1/1000, are added. The whole mixture is separated by capillary electrophoresis and visualized using the Applied Biosystems sequencer.

In Organello Protein Synthesis Protocol:

After extraction, an amount of mitochondria equivalent to 100 µg of proteins is incubated for one hour at 25° C. in 100 µL of IS buffer (5 mM $KH_2PO_4$, 300 mM mannitol, 60 mM KCl, 50 mM HEPES, pH 7.0, 10 mM $MgCl_2$, 10 mM Na malate, 10 mM NADH), 2 mM of GTP, 4 mM of ADP, 2 mM of DTT, 0.1% w/v of BSA, 25 µM of each amino acid except for methionine, and 20 µCi of [$^{35}$S]methionine. During the reaction, the [$^{35}$S]methionine is incorporated into the proteins in the process of being synthesized. The reaction is stopped by adding 1 ml of washing buffer (as described for the preparation of the mitochondria) containing 10 mM of nonradioactive methionine. The mitochondria are then sedimented by centrifugation for 5 min at 12 000×g and stored at −80° C. The equivalent of 20 µg of proteins is then separated on a polyacrylamide gel and the mitochondrial proteins thus labeled during the reaction are then visualized by fluorography.

II. Results

II.1 In vitro Validation of the Trans-Ribozyme Activity of the tRzatp9-L-PKTLS RNA The functionality of the trans-ribozyme/target system was tested in vitro in order to verify the activity of the ribozyme and the retention of this activity after combination with the PKTLS sequence of TYMV.

1) Gene Constructions

The target RNA and the tRzatp9-L-PKTLS RNA were synthesized by in vitro transcription from a PCR product. The atp9 target sequence (SEQ ID No. 6) was amplified by PCR from *Arabidopsis thaliana* DNA with the direct primer 5'-AGCAAGAATTC GAATTGTAATACGACTCACTATAGGT TGTCGAGAT-TCAGTTGGTCTT-3' (SEQ ID No. 7) carrying the T7 phage RNA polymerase promoter (underlined) and the reverse primer 5'-GTACAGAATTCAATGATG-GATTTCGCGCCACA-3' (SEQ ID No. 8). The DNA template for the synthesis of the tRzatp9-L-PKTLS RNA was assembled by means of two consecutive PCR reactions, the first with the primers 5'-ATGAGCTTTTGCGAAATAGCA-GCTAGCATTGAAATAGCATTCAATGCTCATA CTGT-GAACCTACACACTTCCACCTAAGTTCTCG-3' (SEQ ID No. 9) and 5'-TGGTTCCGATGACCCTCGG-3' (SEQ ID No. 10), the second with the primer 5'-AGCAAGAATTC GAATTGTAATACGACTCACTATAGGCCAATACCCT-GATGAGCTTTTGCGAAATAGCAG-3' (SEQ ID No. 11) (T7 phage RNA polymerase promoter underlined) and the primer of sequence SEQ ID No. 10.

2) In vitro Cleavage Tests

In order to be able to visualize its cleavage, the target RNA was synthesized in vitro in radioactive form. It was then incubated with the tRzatp9-L-PKTLS RNA synthesized from the PCR template or with a synthetic RNA (Sigma-Aldrich) corresponding strictly to the sequence of the trans-ribozyme (SEQ ID No. 12; 5'-CCAAUAC-CCUGAUGAGCUUUUGCGAAAUAGCAG-3'). The reaction was tested in the presence of concentrations of $MgCl_2$ that can be found in vivo (1 to 2 mM) (Igamberdiev and Kleczkowski, 2001, *Biochem J.*, 360, 225-231).

The results are represented in FIG. 2. The in vitro tests showed that the tRzatp9 trans-ribozyme, as designed, was capable of cleaving its target under low $MgCl_2$ concentration conditions and that its activity was retained under the same conditions once it was combined with the PKTLS sequence of TYMV by means of the specific linker sequence L in the tRzatp9-L-PKTLS RNA.

II.2. atp9 mRNA Knockdown in Plant Cell Mitochondria in vivo

1) Gene Construction and Plant Cell Transformation

The complete sequence (SEQ ID No. 1) expressing the tRzatp9 trans-ribozyme, the L linker sequence, the PKTLS sequence of TYMV and the cHDV cis-ribozyme was assembled by PCR amplification from the plasmid pCK-SPTYPKTLScHDV with the direct primer (SEQ ID No. 13) 5'-GTACAAAGCTTCCAATACCCTGA-TGAGCTTTTGCGAAATAGCAGCTAGCAT TGAAATAGCATTCAATGCTCATACTGTGAACCTA-CACACTTCCACCTAAGTTCT CG-3' (HindIII site underlined) and the reverse primer 5'-AGCAA GAATTCCTCCCTTAGCCATCCGAGTG-3' (SEQ ID No. 14) (EcoRI site underlined). The fragment obtained was introduced into the plasmid pUCAP (Van Engelen et al., 1995, *Transgenic Res.*, 4, 288-290) between the HindIII and EcoRI sites, and then re-excised with AscI and PacI enzymes and finally cloned between the AscI and PacI sites of the plasmid pER8 (Zuo et al., 2000, *Plant J.*, 24, 265-273), thus generating the plasmid pER8-tRzatp9LPKTLScHDV. The construct was thus inserted into the plasmid pER8 in the expression cassette under the control of the estradiol-inducible XVE promoter.

The final plasmid pER8-tRzatp9LPKTLScHDV was used to transform BY-2 tobacco cells by means of *Agrobacterium tumefaciens*.

2) Analysis of the Expression In and the Importation into Mitochondria of the tRzatp9-L-PKTLS RNA Cultures in liquid suspension were developed from the calluses of *N. tabacum* transformed with the plasmid pER8-tRzatp9LPKTLScHDV. The construct was left silent or was induced with estradiol. Nontransformed cells treated or not treated with estradiol were also used as a control. The cell suspensions were used to isolate mitochondria which were extracted in order to prepare mitochondrial RNA. Total RNA was in addition prepared from the same cells. The expression in and the importation into the mitochondria of the tRzatp9-L-PKTLS RNA were then analyzed by RT-PCR and by nuclease protection of a radioactive antisense probe.

For the RT-PCR analysis, the reverse transcription reaction was carried out with the primer 5'-TGGTTCCGAT-GACCCTCGGA-3' (SEQ ID No. 15) complementary to the 3' end of the PKTLS sequence. For the PCR amplification reaction, this primer was subsequently coupled with the direct primer 5'-CCAATACCCTGATGAGCTTTTG-3' (SEQ ID No. 16) corresponding to the 5' end of the sequence of the tRzatp9 ribozyme. In order to verify the effectiveness of the autocatalytic cleavage of the cHDV cis-ribozyme, similar reactions were carried out with the same direct primer (SEQ ID No. 16) and the reverse primer 5'-CTC-CCTTAGCCATCCGAGTG-3' (SEQ ID No. 17) complementary to the 3' end of the cHDV sequence. In order to test the residual contamination of the mitochondrial samples with cytosolic RNAs, RT-PCR reactions were carried out with the direct primer 5'-ATGAATTCGAATTGTAATAC-GACTGACTA TAGGGCATTTGGTCTAG-3' (SEQ ID No. 18) and the reverse primer 5'-CAGGATC-CTGGGGGGCATTCCGAG-3' (SEQ ID No. 19) making it possible to amplify the cytosolic tRNA$^{Pro}$(UGG) and tRNA$^{Pro}$(AGG). In order to characterize the mitochondrial RNA samples, RT-PCR reactions were carried out with primers specific for mitochondrial tRNA$^{Cys}$(GCA) using the direct primer 5'-GAATTCGGCTAGGTAACATAATG-GAAATG-3' (SEQ ID No. 20) and the reverse primer 5'-GGATCCAGGCCAAGGACGGGGTCG-3' (SEQ ID No. 21).

The results (FIG. 3) showed the presence of the tRzatp9-L-PKTLS RNA in the total RNA fraction and in the mitochondrial RNA fraction originating from the tobacco cells transformed with the plasmid pER8-tRzatp9LPKTLScHDV and induced with estradiol. The identity of the PCR products was verified by cloning and sequencing. Amplification of the tRNAs$^{Pro}$ showed an absence of significant contamination of the mitochondrial fraction with cytosolic RNAs, whereas amplification of tRNA$^{Cys}$ confirmed the identity of the mitochondrial fraction. Control PCR amplifications subsequent to RT-PCR reactions in which the reverse transcriptase was not added did not generate products. Likewise, the absence of amplification products in the reactions carried out with the reverse primer complementary to the 3' end of the cHDV sequence confirmed effective self-cleavage of the cis-ribozyme.

Assays for ribonuclease protection of a radioactive antisense RNA probe were also developed. The antisense probe was synthesized by in vitro transcription from a PCR product. For this, the PKTLS sequence of TYMV was amplified by PCR with the direct primer 5'-ACACTTC-CACCTAAGTTCTCG-3' (SEQ ID No. 22) and a reverse primer carrying the T7 phage RNA polymerase promoter (underlined) 5'-GAATTGTAATACGACTCACTATAGGGTG-GTTCCGATGAC CCTCGG-3' (SEQ ID No. 23). A nonradiolabeled sense transcript of the PKTLS sequence of TYMV was synthesized in the same manner from a PCR product generated with the direct primer 5'-GAATTGTAATACGACTCACTATAGGGACACTTC-CACCTAAGTTCTCG-3' (SEQ ID No. 24) carrying the T7 promoter (underlined) and the reverse primer of sequence SEQ ID No. 15, in order for said transcript to be used as a positive control. In order to test the cytosolic contamination in the mitochondrial fractions, radioactive antisense and nonlabeled sense transcripts corresponding to the cytosolic tRNAs$^{Pro}$ were synthesized in the same way. The PCR template for the antisense tRNA$^{Pro}$ sequence was generated with the direct primer 5'-CATTTGGTCTAGTGGTAT-GATTC-3' (SEQ ID No. 25) and the reverse primer carrying the T7 phage RNA polymerase promoter (underlined) 5'-GAATTGTAATACGACTCACTATAGGGTGGG GGGCATTCCGAGAATC-3' (SEQ ID No. 26). The PCR template for the sense tRNA$^{Pro}$ sequence was generated with the direct primer carrying the T7 phage RNA polymerase promoter (underlined) 5'-GAATTGTAATACGACTCACTATAGGGCATTTGGTC-TAGTGGTATGATTC-3' (SEQ ID No. 27) and the reverse primer 5'-TGGGGGGCATTCCGAGAATC-3' (SEQ ID No. 28).

The assays showed RNase protection of an antisense RNA of the expected size in the presence of total RNA and of mitochondrial RNA of tobacco cells transformed with the plasmid pER8-tRzatp9LPKTLScHDV and induced with estradiol (FIG. 4). The assays with the tRNA$^{Pro}$ probes did not reveal any significant cytosolic contamination.

The RT-PCR and ribonuclease protection experiments therefore showed expression of the tRzatp9-L-PKTLS RNA and importation thereof in vivo in mitochondria of transformed BY-2 tobacco cells induced with estradiol.

The exact 5' and 3' ends of the transcripts resulting from the tRzatp9LPKTLScHDV construct in the transformed cells were analyzed by circularized RNA RT-PCR (CR-RT-PCR). After circularization of the total RNA of transformed cells, a cDNA covering the junction created by the circularization of the tRzatp9-L-PKTLS RNA was synthesized with the primer 5'-AGGTTCACGTATGAGCATTGA-3' (SEQ ID No. 29). A first PCR reaction was carried out with the same primer (SEQ ID No. 29) and the direct primer of sequence SEQ ID No. 22. A nested PCR reaction was then carried out with the primer 5'- ATGCTATTTCAAT-GCTAGCTGCTATTT-3' (SEQ ID No. 30) and the primer 5'-ATCTTTAAAATCGTTAGCTCGCCAGT-3' (SEQ ID No. 31). The products of the second PCR were cloned and sequenced. The sequence of the CR-RT-PCR result is SEQ ID No. 67; the sequence of the excepted result is SEQ ID No. 68; and the key overlapping sequence is SEQ ID No. 69. The sequencing results confirmed that the tRzatp9-L-PKTLS RNA present in the transformed cells indeed had the expected ends, with in particular the CCA triplet at the 3' end of the PKTLS sequence (FIG. 5).

3) Mitochondrial atp9 mRNA Knockdown by the Imported tRzatp9-L-PKTLS RNA

Since the tRzatp9-L-PKTLS RNA is imported into the mitochondria of the transformed tobacco cells, its activity of cleaving its target, i.e. the edited coding sequence of the tobacco atp9 mRNA (SEQ ID No. 32), in the organelles in vivo was analyzed. For this, the atp9 mRNA level was determined by quantitative RT-PCR (qRT-PCR) in the RNA of transformed or nontransformed tobacco cells induced or not induced with estradiol. The reverse transcription was carried out with the primer 5'-GCAAACGATG-CAATAGCTTCGGT-3' (SEQ ID No. 33) and the PCR reaction was carried out with the same primer coupled with the direct primer 5'-TGCTACAATTGCTTCAGCGGGA-3' (SEQ ID No. 34). The nuclear mRNA encoding actin and the mitochondrial mRNA encoding the RPL2 ribosomal protein were used as references. They were amplified by qRT-PCR with the pairs of primers 5'-CGAAGAATTGCATGAG-GAAGGGC-3' (direct) (SEQ ID No. 35)-5'-GCCAGTGGC-CGTACAACAGGT-3' (reverse) (SEQ ID No. 36), and 5'-CTTGCCCGCTTCCAATTGATG-3' (direct) (SEQ ID No. 37)-5'-CTGCCAAGCCGATAGGCGAA-3' (reverse) (SEQ ID No. 38).

The results, represented in FIG. 6, showed that the atp9 mRNA level in the estradiol-induced cells expressing the tRzatp9-L-PKTLS RNA was reduced by 80% (+/−9%) compared with estradiol-induced cells not expressing the tRzatp9-L-PKTLS RNA, demonstrating the directed knockdown of a mitochondrial mRNA in plant cells.

Supplementary analyses by fluorescently labeled primer extension (Fluorescently Labeled Oligonucleotide Extension or FLOE) (Lloyd et al., 2005, *J. Microbiol Methods*, 60, 291-298) were carried out on the RNAs of tobacco cells transformed with the plasmid pER8-tRzatp9LPKTLScHDV and induced or not induced with estradiol, in order to determine whether the reduction in the atp9 mRNA level was indeed due to specific cleavage of the site targeted (SEQ ID No. 32) by the tRzatp9 trans-ribozyme.

The reactions were carried out with the primer 5'-CTAACGGACTTAGAATACGAATAAGAT-3' (SEQ ID No. 39) 5'-labeled with the ROX fluorophore.

The results are represented in FIG. 7. These assays demonstrated two products common to the induced and noninduced cell samples, an RNA of 357 nucleotides probably corresponding to an initial transcript and an RNA of 244 nucleotides corresponding to the mature RNA, but also an RNA of 168 nucleotides specific for the induced cells and corresponding to the product of 3' cleavage of the atp9 mRNA by the tRzatp9 trans-ribozyme imported into the mitochondria.

These results therefore demonstrate that a trans-ribozyme combined with the PKTLS sequence of TYMV is functional in plant cell mitochondria and specifically cleaves its target.

4) Phenotype Induced by the Mitochondrial atp9 mRNA Knockdown Resulting from Cleavage by the Imported tRzatp9-L-PKTLS RNA In organello protein synthesis assays were carried out with mitochondria extracted from tobacco cells transformed with the plasmid pER8-tRzatp9LPKTLScHDV and induced or not induced with estradiol. In accordance with the knockdown of the atp9 mRNA, the translation of the ATP9 protein was reduced on average by 30% in the mitochondria of the induced cells compared with those of the noninduced cells (see FIG. 8). The respiratory activity of the mitochondria isolated from the induced cells was reduced in similar proportions, both at stage IV and at stage III (see FIG. 9). Finally, the cells transformed with the plasmid pER8-tRzatp9LPKTLScHDV and induced with estradiol exhibited delayed growth (see FIG. 10).

EXAMPLE II

Use of the PKTLS Sequence of TYMV for Importing into Plant Cell Mitochondria a Trans Hammerhead Ribozyme Directed Against the mnc1 Mitochondrial RNA In the mitochondrial genome of *Arabidopsis thaliana* (gi accession number: 26556996 or gi accession number: 49256807 in the Genbank database), the sequence encoding the mnc1 RNA (nucleotides 159350-159643 in antisense) is in a long intergenic region between the mttB gene (orfX) and exon 1 of the nad4 gene, in the antisense orientation relative to these protein genes. FIG. 11 (SEQ ID No. 40) shows the elements of the recombinant RNA (polyribonucleotide) which make it possible to import into plant cell mitochondria a trans hammerhead ribozyme directed against the mnc1 mitochondrial RNA. The trans hammerhead ribozyme directed against the mnc1 RNA (tRzmnc1) is combined with the PKTLS sequence of TYMV by means of a specific linker sequence (L) developed by bioinformatics with the MFOLD software.

I. In vitro Validation of the Trans-Ribozyme Activity of the tRzmnc1-L-PKTLS RNA Before initiating the in vivo approach, the functionality of the trans-ribozyme/target system was established in vitro, as previously (cf. Example I), in order to verify the activity of the ribozyme and the retention of this activity after combination with the PKTLS sequence of TYMV.

1) Gene Constructions

The target RNA (SEQ ID No. 41) and the tRzmnc1-L-PKTLS RNA were synthesized by in vitro transcription from a PCR product. The mnc1 mitochondrial RNA sequence of *A. thaliana* (SEQ ID No. 41) used as target for the tRzmnc1 trans-ribozyme was amplified by PCR from *A. thaliana* DNA with the direct primer 5'-AGCAAGAATTC GAATTGTAATACGACTCACTATAGGTGCTTTGCT-CGCTCCGAC-3' (SEQ ID No. 42) carrying the T7 phage RNA polymerase promoter (underlined) and the reverse primer 5'-GTACAGAATTCGTGACGTCTCTTGCTGGG-3' (SEQ ID No. 43). The DNA template for the synthesis of the tRzmnc1-L-PKTLS RNA (SEQ ID No. 40) was assembled by means of two consecutive PCR reactions, starting from the plasmid pCK-SPTYPKTLScHDV (described above) containing the PKTLS sequence of TYMV, the first with the primer 5'-GAGCT-TTTGCGAAACTGGCCACTTGCCTATAGCACAATC-TATTCATGAACAATAGAAGATACACTTCCAC-CTAAGTTCTCG-3' (SEQ ID No. 44) and the primer of sequence SEQ ID No. 10, the second with the primer 5'-AGCAAGAATTC GAATTGTAATACGACTCACTATAGGAATCCAGCC TGATGAGCTTTTGCGAAACTGGCC-3' (SEQ ID No. 45) (T7 phage RNA polymerase promoter) and the primer of sequence SEQ ID No. 10.

2) In vitro Cleavage Tests

In order to be able to visualize its cleavage, the mnc1 target RNA was synthesized in vitro in a radioactive form. It was then incubated with the tRzmnc1-L-PKTLS RNA synthesized from the PCR matrix or with a synthetic RNA (ordered from Sigma-Aldrich) corresponding strictly to the sequence of the tRzmnc1 trans-ribozyme (5'-AAUCCAGC-CUGAUGAGCUUUUGCGAAACUGGCC-3'; SEQ ID No. 46). The reaction was tested in the presence of concentrations of $MgCl_2$ that can be found in vivo (Igamberdiev and Kleczkowski, 2001, *Biochem J.*, 360, 225-231).

The in vitro tests showed that the tRzmnc1 trans-ribozyme as designed was capable of cleaving its target under low $MgCl_2$ conditions (FIG. 12A) and that its activity was retained under the same conditions once it was combined with the PKTLS sequence of TYMV by means of the specific linker sequence L in the tRzmnc1-L-PKTLS RNA (FIG. 12B).

II. Cleavage of the mnc1 RNA in Plant Cell Mitochondria in vivo

1) Gene Construction

The complete DNA sequence (SEQ ID No. 47) containing the sequences expressing the tRzmnc1 trans-ribozyme, the linker sequence L, the PKTLS sequence of TYMV and the cHDV cis-ribozyme was assembled by PCR amplification from the plasmid pCK-SPTYPKTLScHDV (see Example I) with the direct primer 5'-GTACA AAGCTTAATCCAGCCTGATGAGCTTTTGCGAAA-CTGGCCACTTGCCTATA GCACAATCTATTCAT-GAACAATAGAAGATACACTTCCACCTAAGTTCTCG-3' (SEQ ID No. 48) (HindIII site underlined) and the reverse primer of sequence SEQ ID No. 14). The fragment obtained was introduced into the plasmid pUCAP (Van Engelen et al., 1995, *Transgenic Res.* 4, 288-290) between the HindIII and EcoRI sites, and then re-excised with the AscI and PacI enzymes and finally cloned between the AscI and PacI sites of the plasmid pER8 (Zuo et al., 2000, *Plant J.*, 24, 265-273), generating the plasmid pER8-tRzmnc1LPKTLScHDV. The construct was thus inserted into the plasmid pER8 in the expression cassette under the control of the estradiol-inducible XVE promoter.

2) Genetic Transformation of Plants

The final plasmid pER8-tRzmnc1LPKTLScHDV was used to transform *A. thaliana* influorescences by means of *A. tumefaciens* ("floral dip", Clough and Bent, 1998, *Plant J.,* 16, 735-743). Seeds were harvested for genotyping.

EXAMPLE III

Use of the PKTLS Sequence of TYMV for Importing into Plant Cell Mitochondria a Trans Hammerhead Ribozyme Directed Against the or78 Mitochondrial RNA A transcript of 4.3 kb (gi accession number: 14582613 in the Genbank database) of unknown function and carrying an untranslated open reading frame (orf78) was previously characterized in potato (*Solanum tuberosum*) mitochondria (Siqueira et al., 2001, *Biochim Biophys Acta*, 1520, 203-211). A part of this transcript located outside the ORF (Open Reading Frame) is conserved in intergenic regions of the mitochondrial genomes of other species, such as *A. thaliana* or *Brassica campestris*, in the antisense orientation relative to known genes.

A trans-ribozyme strategy was developed against the *S. tuberosum* transcript (or78). FIG. 13 (SEQ ID No. 49) shows the elements of the polyribonucleotide (recombinant RNA) developed for this strategy. The trans hammerhead ribozyme directed against the or78 RNA (tRzor78) is combined with the PKTLS sequence of TYMV by means of a specific linker sequence (L) developed by bioinformatics using the MFOLD software.

I. In vitro Validation of the Trans-Ribozyme Activity of the tRzor78-L-PKTLS RNA The functionality of the trans-ribozyme/target system was established in vitro, as previously (cf. Example I), in order to verify the activity of the ribozyme and the retention of this activity after combination with the PKTLS sequence of TYMV.

1) Gene Constructions

The target RNA (SEQ ID No. 50) and the tRzor78-L-PKTLS RNA (SEQ ID No. 49) were synthesized by in vitro transcription from a PCR product. The *Solanum tuberosum* or78 mitochondrial RNA sequence (corresponding to nucleotides 987-1490, sense orientation in the sequence identified under gi accession number: 14582613 in the Genbank database; SEQ ID No. 50) used as target for the tRzor78 trans-ribozyme was amplified by PCR from *S. tuberosum* mitochondrial DNA with the direct primer 5'-AGCAAGAATTC GAATTGTAATACGACTCACTATAGGC-CGATCTCAAGCTGGATG-3' (SEQ ID No. 51) carrying the T7 phage RNA polymerase promoter (underlined) and the reverse primer 5'-GTACAGAATTCTTATCAACT-CATAATAAGTAAGGC-3' (SEQ ID No. 52). The DNA template for the synthesis of the tRzor78-L-PKTLS RNA (SEQ ID No. 49) was assembled by means of two consecutive PCR reactions, starting from the plasmid pCK-SPTYP-KTLScHDV (described above) containing the PKTLS sequence of TYMV, the first with the primer 5'-AT-GAGCTTTTGCGAAACGTTGTGACCAGCAGCTGC-CAGTAACACACCTACGTGCG CTGCCAAACACTTC-CACCTAAGTTCTCG-3' (SEQ ID No. 53) and the primer of sequence SEQ ID No. 10, the second with the primer 5'-AGCAAGAATTC GAATTGTAATACGACTCACTATAGGCCTATGTC CTGATGAGCTTTTGCGAAACGTTGT-3' (SEQ ID No. 54) (T7 phage RNA polymerase promoter underlined) and the primer of sequence SEQ ID No. 10.

2) In vitro Cleavage Tests

In order to be able to visualize its cleavage, the or78 target RNA was synthesized in vitro in radioactive form. It was then incubated with the tRzor78-L-PKTLS RNA synthesized from the PCR template or with a synthetic RNA (ordered from Sigma-Aldrich) corresponding strictly to the sequence of the tRzor78 trans-ribozyme (5'-CCUAUGUC-CUGAUGAGCUUUUGCGAAACGUUGU-3') (SEQ ID No. 55). The reaction was tested in the presence of concentrations of $MgCl_2$ that can be found in vivo (Igamberdiev and Kleczkowski, 2001, mentioned above).

The in vitro tests showed that the tRzor78 trans-ribozyme was capable of cleaving its target under low $MgCl_2$ conditions (FIG. 14A) and that its activity was retained under the same conditions once it was combined with the PKTLS sequence of TYMV by means of the specific linker sequence L in the tRzor78-L-PKTLS RNA (FIG. 14B).

II. Cleavage of the or78 RNA in Plant Cell Mitochondria in vivo

1) Gene Construction

The DNA sequence (SEQ ID No. 56) expressing the tRzor78 trans-ribozyme, the linker sequence L, the PKTLS sequence of TYMV and the cHDV cis-ribozyme is assembled by PCR amplification from the plasmid pCK-SPTYPKTLScHDV (see Example I) with the direct primer 5'-GTACA<u>AAGCTT</u>CCTATGTCCTGA-TGAGCTTTTGCGAAACGTTGTGACCAGCAGCT GCCAGTAACACACCTACGTGCGCTGCCAAACACT-TCCACCTAAGTTCTCG-3' (SEQ ID No. 57) (HindIII site underlined) and the reverse primer of sequence SEQ ID No. 14. The fragment obtained is introduced into the plasmid pUCAP (Van Engelen et al., 1995, mentioned above) between the HindIII and EcoRI sites, and then re-excised with the AscI and PacI enzymes and finally cloned between the AscI and PacI sites of the plasmid pER8 (Zuo et al., 2000, mentioned above), generating the plasmid pER8-tRzor78LPKTLScHDV. The construct is then inserted into the plasmid pER8 in the expression cassette under the control of the estradiol-inducible XVE promoter.

2) Genetic Transformation of Plants

The final plasmid pER8-tRzor78LPKTLScHDV was used to transform internodal sections of *S. tuberosum* by means of *A. tumefaciens* (Millam, 2006, *Methods Mol. Biol.*, 344, 25-36).

EXAMPLE IV

In vitro Comparison of Cleavage Efficiency Between 2 Types pf Trans Hammerhead Ribozymes Directed Against the or78 Mitochondrial RNA 1) Materials and Methods 4 different RNA constructs consisting of a trans hammerhead ribozyme directed against the or78 mitochondrial RNA (SEQ ID No. 50), of a linker sequence (L) and of the PKTLS sequence of TYMV (PKTLS) (see FIG. 15) were tested with regard to their efficiency in cleaving the or78 mitochondrial RNA (target RNA):

tRzor78-L-PKTLS (SEQ ID No. 49): the trans-ribozyme (tRzor78) of this construct has, in its stem-loop II, a loop consisting of 4 nucleotides (UUUU) and a helix II consisting of 2 nucleotide pairs (G-C and C-G), and contains no tertiary stabilizing structure; 8 contiguous nucleotides hybridize to the target RNA in the 5' position of the trans-ribozyme (helix I), and 7 contiguous nucleotides hybridize to the target RNA in the 3' position (helix III) of the trans-ribozyme;

tRzor78TS-L-PKTLS (SEQ ID No. 58): the trans-ribozyme (tRzor78TS) of this construct is tertiary stabilized by means of the addition of an additional stem-loop (compared with the tRzor78 trans-ribozyme) in the 5' position, which establishes tertiary interactions with stem-loop II. It has, in its stem-loop II, a loop consisting of 4 nucleotides (GAAA) and a helix II consisting of 4 nucleotide pairs (G-C, U-A, C-G, G-C); 6 contiguous nucleotides hybridize to the target RNA in the 5' position (helix I) and in the 3' position (helix III) of the trans-ribozyme;

tRzor78/6+6-L-PKTLS (SEQ ID No. 59): the trans-ribozyme (tRzor78/6+6; at positions 2 and 32) of this construct has, in its stem-loop II, a loop consisting of 4 nucleotides (UUUU) and a helix II consisting of 2 nucleotide pairs (G-C and C-G), and does not contain a tertiary stabilizing structure; 6 contiguous nucleotides hybridize to the target RNA in the 5' position (helix I) and in the 3' position (helix III) of the trans-ribozyme;

tRzor78TS/8+7-L-PKTLS (SEQ ID No. 60): the trans-ribozyme (tRzor78TS/8+7) of this construct is tertiary stabilized by means of the addition of an additional stem-loop (compared with the tRzor78 trans-ribozyme) in the 5' position, which establishes tertiary interactions with stem-loop II. It has, in its stem-loop II, a loop consisting of 4 nucleotides (GAAA) and a helix II consisting of 4 nucleotide pairs (G-C, U-A, C-G, G-C); 8 contiguous nucleotides hybridize to the target RNA in the 5' position of the trans-ribozyme (helix I), and 7 contiguous nucleotides hybridize to the target RNA in the 3' position of the trans-ribozyme (helix III).

The synthesis of the or78 target RNA (SEQ ID No. 50) and of the tRzor78-L-PKTLS RNA (SEQ ID No. 49) by in vitro transcription from a PCR product was carried out as previously described (see Example III.I.1). The same strategy was developed in order to produce the other three recombinant ribozyme-L-PKTLS RNAs. The DNA templates for the synthesis of the tRzor78TS-L-PKTLS, tRzor78/6+6-L-PKTLS and tRzor78TS/8+7-L-PKTLS RNAs were assembled by means of two consecutive PCR reactions, starting from the plasmid pCK-SPTYPK-TLScHDV (described above) containing the PKTLS sequence of TYMV (the T7 phage RNA polymerase promoter is underlined):

for the synthesis of tRzor78TS-L-PKTLS, the first PCR was carried out with the direct primer 5'-GTCG-GAAACGACGAAACGTTGACTTGCCTATAGCA-CAATCTATTCATGAA CAATAGAAGATACACT-TCCACCTAAGTTCTCG-3' (SEQ ID No. 61) and the second PCR was carried out with the direct primer 5'-AGCAAGAATTC GAATTGTAATACGACTCACTATAGG-CTAAGGCAAACGCT ATGCTATGTCCTGAT-GAGTCGGAAACGACGAAACGTTG-3' (SEQ ID No. 62);

for the synthesis of tRzor78/6+6-L-PKTLS, the first PCR was carried out with the direct primer 5'-GAT-GAGCTTTTGCGAAACGTTGGAGAAGAAGCT-GCCAGTAACACACC TACGTGCGCTGC-CAAACACTTCCACCTAAGTTCTCG-3' (SEQ ID No. 63) and the second PCR was carried out with the direct primer 5'-AGCAAGAATTC GAATTGTAATACGACTCACTATAGGTATGTCC-TGATGAGCTTTTGCGAAACGTTG-3' (SEQ ID No. 64);

for the synthesis of tRzor78TS/8+7-L-PKTLS, the first PCR was carried out with the direct primer 5'-TCG-GAAACGACGAAACGTTGTACTTGAATATAGCA-CAATCTATTCA TGAACAAAAGAAGATACACT-TCCACCTAAGTTCTCG-3' (SEQ ID No. 65) and the second PCR was carried out with the direct primer 5'-AGCAAGAATTC GAATTGTAATACGACTCACTATAGGCTAA-GGCAAACGCT ATGCCCTATGTCCTGAT-GAGTCGGAAACGACGAAACGTTGT-3' (SEQ ID No. 66).

The primer 5'-TGGTTCCGATGACCCTCGG-3' (SEQ ID No. 10), which is complementary to the 3' end of PKTLS, was used as a reverse primer for all the PCR reactions.

2) In vitro Cleavage Tests

The cleavage activity of the various trans hammerhead ribozymes combined with a linker sequence (L) and with the PKTLS sequence of TYMV was tested in a reaction medium containing 15 nM of nonradioactive or78 target RNA, 50 fmol (30 000 cpm) of or78 target RNA labeled with [$^{32}$P], 150 nM of ribozyme-L-PKTLS RNA and 50 mM of Tris-HCl buffer at pH 7.5. The reaction medium was first brought to 75° C. for 2 min, and cooled very slowly (0.3° C. per min) to 25° C., in order to denature the structures which form in the target RNA and the catalytic RNA during the transcription by the T7 RNA polymerase and to promote the formation of the specific trans-ribozyme/target RNA complex. The actual cleavage reaction was carried out by incubation of the reaction medium for 1 to 5 hours at 25° C., in the presence of various concentrations of $MgCl_2$. The cleavage products were then separated by electrophoresis on an 8% or 10% (w/v) polyacrylamide/8M urea gel in 90 mM Tris-borate buffer containing 2 mM of EDTA (1×TBE). The gels were fixed, dried and analyzed by autoradiography.

2) Results

The or78 target RNA was synthesized in vitro in radioactive form in order to be able to visualize its cleavage. It was then incubated with the tRzor78-L-PKTLS (SEQ ID No. 49), tRzor78TS-L-PKTLS (SEQ ID No. 58), tRzor78/6+6-L-PKTLS (SEQ ID No 59) and tRzor78/8+7-L-PKTLS (SEQ ID No. 60) recombinant RNAs synthesized by in vitro transcription from the corresponding PCR templates. The reaction was tested in the presence of concentrations of $MgCl_2$ that can be found in vivo (1 mM).

The results are represented in FIG. 16. These results show that all the recombinant RNAs tested cleave the or78 target RNA both in the presence of 1 mM $MgCl_2$ and in the absence of $Mg^{2+}$, which is particularly favorable for in vivo use.

However, the in vitro comparative tests showed that the tRzor78-L-PKTLS recombinant RNA had a greater cleavage efficiency compared with that of the other three recombinant RNAs. This greater efficiency was found both in the presence of 1 mM $MgCl_2$ and in the absence of $Mg^{2+}$.

The invention claimed is:

1. A polyribonucleotide comprising, from its 5' end to its 3' end, (a) a trans hammerhead ribozyme consisting of from 24 to 100 nucleotides directed against a plant mitochondrial RNA and (b) a tRNA-like structure aminoacylatable with valine from the genome of Turnip yellow mosaic virus (TYMV),
   wherein the last nucleotide in the 3' position of said tRNA-like structure is an adenine,
   said trans hammerhead ribozyme recognizes a target sequence contained in said plant mitochondrial RNA and is capable of cleaving the mitochondrial RNA,
   said trans hammerhead ribozyme hybridizes to said plant mitochondrial RNA at between 3 to 50 contiguous nucleotides in the 5' position of said trans hammerhead ribozyme and at between 3 to 50 contiguous nucleotides in the 3' position of said trans hammerhead ribozyme, and
   said trans hammerhead ribozyme and said tRNA-like structure are separated by an upstream pseudoknot from the genome of Turnip yellow mosaic virus (TYMV).

2. The polyribonucleotide as claimed in claim 1, wherein said trans hammerhead ribozyme has, in its stem-loop II, a loop consisting of 4 nucleotides, and a helix II consisting of 2 nucleotide pairs.

3. The polyribonucleotide as claimed in claim 1, wherein said trans-hammerhead ribozyme and said upstream pseudoknot are separated by a linker RNA sequence.

4. The polyribonucleotide as claimed in claim 1, wherein said tRNA-like structure aminoacylatable with valine is combined, in the 3' position, with a ribozyme that is self-cleaving in cis in the 5' position (cis-ribozyme).

5. The polyribonucleotide as claimed in claim 1, wherein the plant mitochondrial RNA is chosen from the messenger RNA of the atp9 gene, the mnc1 RNA and the or78 RNA.

6. The polyribonucleotide as claimed in claim 4, wherein said cis-ribozyme is derived from the genome of a virus.

7. The polyribonucleotide as claimed in claim 1, wherein the polyribonucleotide is chosen from the sequences SEQ ID NO: 2, 40, 49, 58, 59 and 60.

8. A polydeoxyribonucleotide expressing the polyribonucleotide of claim 1.

9. The polydeoxyribonucleotide of claim 8, wherein the polydeoxyribonucleotide is selected from the group of sequences consisting of SEQ ID NO: 1, 47 and 56.

10. A recombinant expression cassette comprising the polydeoxyribonucleotide of claim 8 under the control of an appropriate transcription promoter.

11. The expression cassette as claimed in claim 10, wherein said promoter is an inducible promoter, a pollen-specific promoter, or an anther-specific promoter.

12. A recombinant vector—comprising the polydeoxyribonucleotide of claim 8.

13. A host cell comprising the recombinant vector of claim 12.

14. The host cell as claimed in claim 13, wherein the host cell is a plant cell.

15. A plant genetically transformed with at least one polydeoxyribonucleotide of claim 8.

16. A method of obtaining a transgenic plant having cytoplasmic male sterility comprising the following steps:
   a) obtaining a plant cell comprising the expression cassette of claim 10 comprising a sequence expressing a hammerhead ribozyme directed against atp9 mRNA, mnc1 RNA or or78 RNA, and
   b) regenerating, from the plant cell obtained in step a), a transgenic plant expressing said hammerhead ribozyme.

17. A transgenic plant obtained by the method of claim 16.

18. The polyribonucleotide as claimed in claim 1, wherein said trans hammerhead ribozyme consists of from 30 to 40 nucleotides.

19. The polyribonucleotide as claimed in claim 6, wherein said cis-ribozyme is derived from the genome of a Hepatitis Delta virus (HDV).

20. The recombinant expression cassette of claim 10, wherein said promoter is functional in plant cells.

21. The polyribonucleotide as claimed in claim 1, wherein said plant mitochondrial RNA is from a plant family selected from the group consisting of Poaceae, Papillonaceae, Cruciferae, Umbelliferae, Solanaceae, Leguminosae, Labiatae and Asteraceae.

22. The polyribonucleotide as claimed in claim 1, wherein said plant mitochondrial RNA is from a plant family selected from the group consisting of corn, wheat, barley, rye, triticale, oats, rapeseed, cabbage, tobacco, pea, tomato, alfalfa, beetroot, sunflower, soya and rice.

23. The polyribonucleotide as claimed in claim 1, wherein said plant mitochondrial RNA is from a Solanaceae.

24. The polyribonucleotide as claimed in claim 2, wherein said plant mitochondrial RNA is from a plant family selected from the group consisting of Poaceae, Papillonaceae, Cruciferae, Umbelliferae, Solanaceae, Leguminosae, Labiatae and Asteraceae.

25. The polyribonucleotide as claimed in claim 2, wherein said plant mitochondrial RNA is from a plant family selected from the group consisting of corn, wheat, barley, rye, triticale, oats, rapeseed, cabbage, tobacco, pea, tomato, alfalfa, beetroot, sunflower, soya and rice.

26. The polyribonucleotide as claimed in claim 2, wherein said plant mitochondrial RNA is from a Solanaceae.

27. The polyribonucleotide as claimed in claim 1, wherein said plant mitochondrial RNA is a messenger RNA.

28. The polyribonucleotide as claimed in claim 1, wherein said plant mitochondrial RNA is a noncoding RNA.

29. The polyribonucleotide as claimed in claim 1, wherein said trans hammerhead ribozyme hybridizes to said mitochondrial RNA at between 5 to 10 contiguous nucleotides in the 5' position of said trans-ribozyme and at between 5 to 10 contiguous nucleotides in the 3' position of said trans-ribozyme.

30. The polyribonucleotide as claimed in claim 3, wherein said linker RNA sequence consists of 35 to 40 nucleotides.

* * * * *